(12) United States Patent
Burnett et al.

(10) Patent No.: US 12,040,062 B2
(45) Date of Patent: Jul. 16, 2024

(54) SYSTEMS AND METHODS FOR REDUCING PATIENT READMISSION TO ACUTE CARE FACILITIES

(71) Applicant: Saiva, Inc., Los Altos, CA (US)

(72) Inventors: Karyn Burnett, Virginia Beach, VA (US); Jaikumar Ramanathan, Saratoga, CA (US); Guy Katsav, Los Altos, CA (US); Jason Strober, Los Altos Hills, CA (US)

(73) Assignee: SAIVA, INC., Mountain View, CA (US)

(*) Notice: Subject to any disclaimer, the term of this patent is extended or adjusted under 35 U.S.C. 154(b) by 353 days.

(21) Appl. No.: 17/165,842

(22) Filed: Feb. 2, 2021

(65) Prior Publication Data

US 2021/0241871 A1 Aug. 5, 2021

Related U.S. Application Data

(60) Provisional application No. 63/069,674, filed on Aug. 24, 2020, provisional application No. 62/969,593, filed on Feb. 3, 2020.

(51) Int. Cl.
*G16H 15/00* (2018.01)
*G16H 10/60* (2018.01)
(Continued)

(52) U.S. Cl.
CPC .......... *G16H 15/00* (2018.01); *G16H 10/60* (2018.01); *G16H 40/20* (2018.01); *G16H 50/20* (2018.01);
(Continued)

(58) Field of Classification Search
None
See application file for complete search history.

(56) References Cited

U.S. PATENT DOCUMENTS

| 2007/0073555 A1* | 3/2007 | Buist | G16H 40/20 600/300 |
| 2011/0313788 A1* | 12/2011 | Amland | G16H 50/20 705/3 |

(Continued)

FOREIGN PATENT DOCUMENTS

WO WO-2015195836 A2 * 12/2015 ......... G06F 19/3431

OTHER PUBLICATIONS

C. Obotu, Akor Solomon, Uganneya A. Solomon PhD., and Ikese Christopher Ogezi. "Evaluative Study of Digital Record Management System in the Hospitals in Minna Metropolis. (A Case Study of General Hospital Minna, Niger State. Nigeria)." Library Philosophy and Practice (Year: 2018).*

(Continued)

*Primary Examiner* — Amber A Misiaszek
(74) *Attorney, Agent, or Firm* — Morgan, Lewis & Bockius LLP

(57) ABSTRACT

Methods and systems for generating a report that ranks patients at risk for readmission to an acute care facility from a post-acute care facility. A system receives, from the post-acute care facility, patient data for a plurality of patients. The system inputs the patient data into a risk machine-learning system that was previously trained using historical patient data and data reflecting any readmissions from one or more post-acute care facilities to one or more acute care facilities. The system determines, by the risk machine-learning system, a risk score for each patient. Each risk score represents risk of a respective patient being readmitted to an acute care facility from the post-acute care facility. The system further generates the report. The report including a list of at least a subset of patients from the plurality of patients ranked from the patient with the highest risk to the lowest risk of readmission.

18 Claims, 15 Drawing Sheets

(51) Int. Cl.
*G16H 40/20* (2018.01)
*G16H 50/20* (2018.01)
*G16H 50/30* (2018.01)
*G16H 50/70* (2018.01)
*G16H 70/60* (2018.01)

(52) U.S. Cl.
CPC ............ *G16H 50/30* (2018.01); *G16H 50/70* (2018.01); *G16H 70/60* (2018.01)

(56) References Cited

U.S. PATENT DOCUMENTS

| | | | |
|---|---|---|---|
| 2012/0303378 A1* | 11/2012 | Lieberman | G06Q 40/08 |
| | | | 705/2 |
| 2013/0197942 A1* | 8/2013 | Chiu | G16H 40/67 |
| | | | 705/3 |
| 2013/0262357 A1 | 10/2013 | Amarasingham et al. | |
| 2015/0213225 A1* | 7/2015 | Amarasingham | G16H 50/30 |
| | | | 705/2 |
| 2016/0285876 A1* | 9/2016 | Perez | G16H 10/60 |
| 2016/0300033 A1* | 10/2016 | Duke | G16H 50/30 |
| 2017/0061093 A1* | 3/2017 | Amarasingham | G16H 10/60 |

OTHER PUBLICATIONS

Saiva, Inc., International Search Report and Written Opinion, PCT/US2021/016559, dated May 11, 2021, 11 pgs.
Saiva, Inc., International Preliminary Report on Patentability, PCT/US2021/016559, dated Jul. 28, 2022, 8 pgs.

* cited by examiner

Saiva Hospitalization Risk Report

Prepared for Northbrook Oaks Facility 1/29/2020 03:56AM EST

| Resident MRN | Today's Rank | Yesterday's Rank | Days on Report | Initial Admission Date | Date of Last Transfer |
|---|---|---|---|---|---|
| 1111 (Mr. Jones) | 1 | N/A | 1 | 1/25/2019 | 1/27/2019 |
| 2222 (Mrs. Smith) | 2 | 3 | 13 | 1/24/2019 | 1/24/2019 |
| 3333 (Mrs. Reed) | 3 | 5 | 5 | 1/26/2019 | 1/30/2019 |
| 4444 (Mrs. Dan) | 4 | 2 | 15 | 1/26/2019 | 1/27/2019 |
| 5555 (Mrs. Forest) | 5 | 1 | 27 | 1/28/2019 | 1/26/2019 |
| 6666 (Mr. Reed) | 6 | 4 | 43 | 1/24/2019 | 1/27/2019 |
| 7777 (Mrs. Moler) | 7 | 6 | 8 | 1/16/2019 | 1/16/2019 |
| 8888 (Mrs. Torres) | 8 | N/A | 1 | 1/22/2019 | 1/18/2019 |
| 9999 (Mr. Samson) | 9 | 10 | 5 | 1/17/2019 | 1/24/2019 |
| 1234 (Mr. Ferg) | 10 | 8 | 4 | 1/26/2019 | 1/30/2019 |
| 2345 (Ms. Lee) | 11 | 9 | 33 | 1/29/2019 | 1/25/2019 |
| 3456 (Mr. Spears) | 12 | 12 | 7 | 1/21/2019 | 1/29/2019 |
| 4567 (Mr. Dean) | 13 | 11 | 9 | 1/28/2019 | 1/17/2019 |
| 5678 (Mr. Johnson) | 14 | 13 | 2 | 1/18/2019 | 1/23/2019 |
| 6789 (Ms. Spice) | 15 | 7 | 10 | 1/17/2019 | 1/28/2019 |

Figure 5

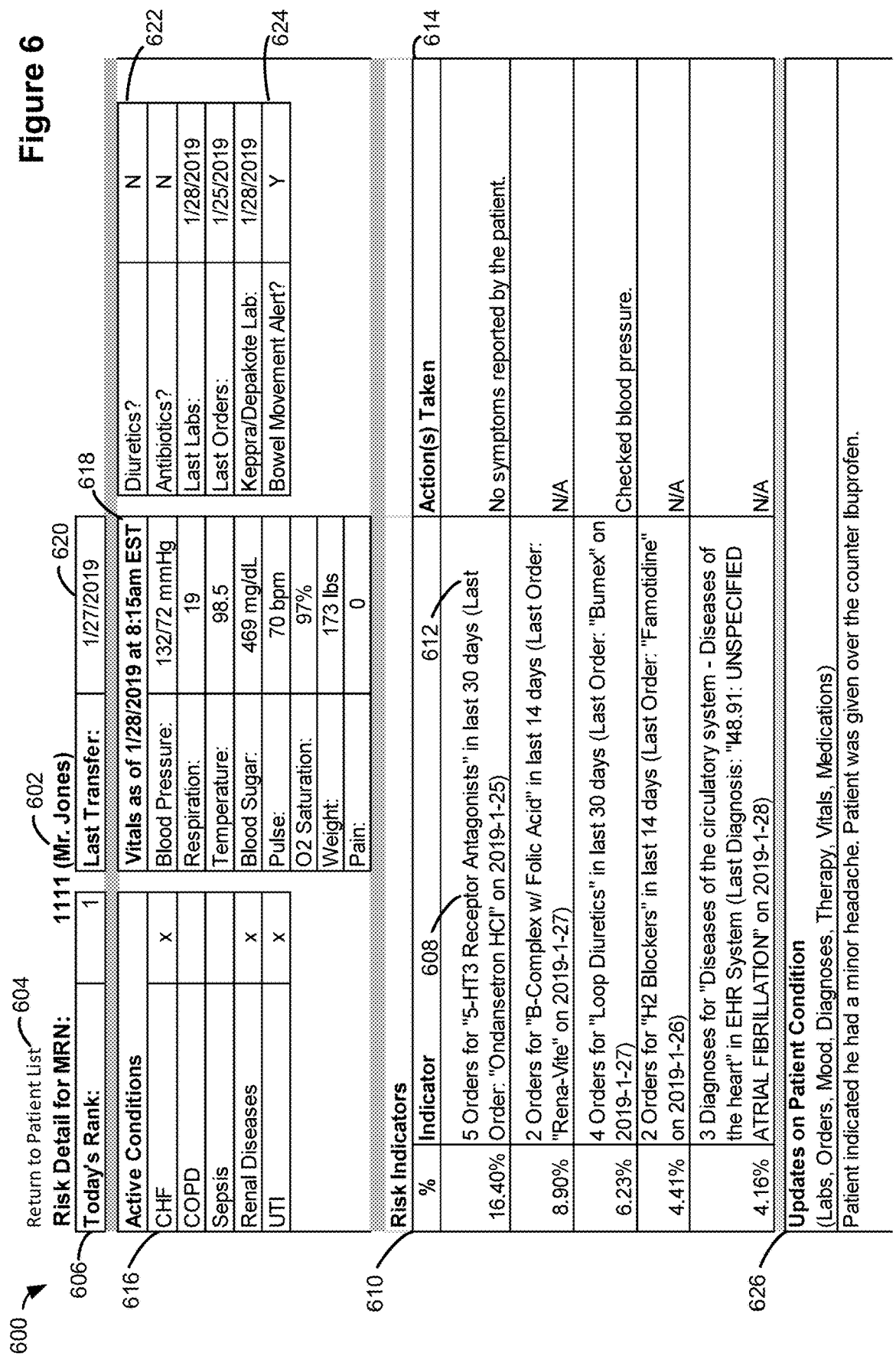

700
(Cont.)

718
Determine, by the risk machine-learning system, a risk score for each patient of the plurality of patients based on each patient's patient data, wherein each risk score represents risk of a respective patient being readmitted to an acute care facility from the post-acute care facility.

720
Generate, for display, the report comprising a list of at least a subset of patients from the plurality of patients, where the list is ranked from the patient with the highest risk of readmission to the patient with the lowest risk of readmission.

722
The report includes respective patient risk scores for each of the patients in the subset of patients.

724
For each patient of the subset of patients, determining one or more risk features that contributed to that patient's respective risk score, wherein the report includes one or more respective risk features for each of the subset of patients.

726
For each of the one or more risk features, determining a risk feature score indicating how much that respective risk feature contributed to the risk score, wherein the report includes, for each of the respective one or more risk features, that respective risk feature's risk feature score and ranks the one or more risk features by their respective risk feature scores from the highest score to the lowest.

728
The one or more risk features that contributed to that patient's respective risk score include a respective explanation and the report includes a portion of the respective explanation for the one or more risk features.

730
The report includes one or more conditions for each of the plurality of patients.

732
The report includes patient data for each of the plurality of patients.

Figure 7B

700 (Cont.)

720 (Cont.)

722 (Cont.)

724 (Cont.)

734
The report includes one or more note entry fields configured to receive input from a caregiver device.

736-a
Receiving an input into a note entry field of the one or more note entry fields; and

736-b
In response to receiving the input into the note entry field, updating the patient data.

738-a
The report includes one or more notification entry fields for receiving user defined notification requests; and

738-b
Receiving a user defined notification request into a notification entry field of the one or more notification entry fields; and

738-c
in response to receiving the user defined notification request, generating a notification event based on the user defined notification request, wherein a notification is provided upon occurrence of the notification event.

740
The notification event includes determining that a subsequent determined risk score for a respective patient is above a user defined risk threshold.

742
The notification event includes a user specified time.

744
The notification event includes a trigger based on an occurrence of one or more patient events.

746
Generating the report comprises, preparing a separate detailed report for each patient of the subset of patients, where each detailed report for a respective patient of the subset of patients comprises that respective patient's one or more risk features and corresponding one or more risk feature scores.

748
The subset of patients is determined based on the plurality of patients with risk scores greater than a risk threshold.

750
The subset of patients comprises a predetermined number of patients with the highest risk scores from the plurality of patients.

752
The subset of patients comprises a predetermined number of patients that have been algorithmically determined.

754
The report comprises historical risk scores for each of the subset of patients.

756
Displaying the report on a remote device.

758
Sending the report to a remote device for display.

760
The report is configured to display on an application installed on a remote device.

762
The report is a spreadsheet.

720 (Cont.)

764-a
Determine whether the risk score for a respective patient of the subset of patients is above a notification threshold; and

764-b
in response to determining that the risk score is above the notification threshold, providing a notification to a medical practitioner of the post-acute care facility to follow up with the patient.

766
Periodically retraining the risk machine-learning system as new patient data, and data reflecting any readmissions from one or more post-acute care facilities to one or more acute care facilities, is collected.

768-a
Before receiving patient data for a plurality of patients, receiving historical patient data from at least one healthcare recording database;

768-b
extracting training data from the historical patient data;

768-c
utilizing the training data to train multiple risk machine-learning systems;

768-d
selecting a risk machine-learning system of the multiple risk machine-learning systems that respectively determined risk scores above a predetermined accuracy rate; and

768-e
storing the risk machine-learning system.

770-a
extracting training data from the historical patient data includes extracting at least validation data; and

770-b
before storing the risk machine-learning system, inputting the validation data into the machine-learning system;

770-c
determining, by the risk machine-learning system, validation scores based on the validation data; and

770-d
Updating the risk machine-learning system based on validation scores.

Figure 7E

John Doe
February 28, 2020 | Facility 69 | MRN 12345 | Room 34A | Rank 2 ← 902

OVERVIEW
60 yr old | Male | Race: White | Primary Doc
Last Transfer

RISK CONDITIONS 808
Sepsis
Diabetes

VITALS 804

| | | |
|---|---|---|
| Blood Pressure | 103/62 mmHg | 10/28/2020 10:47PM |
| Blood Sugar | | |
| O2 Saturation | 85 | 10/28/2020 10:47PM |
| Pain | 5 | 10/28/2020 08:15PM |
| Pulse | 115 bpm | 10/28/2020 10:47PM |
| Respiration | 18 | 10/28/2020 10:47PM |
| Temperature | 98 | 10/28/2020 10:47PM |
| Weight | 168 lbs | 10/28/2020 02:58PM |

RISK DIAGNOSIS
2 weeks ago SEPSIS, UNSPECIFIED ORGANISM
2 weeks ago MALIGNANT NEOPLASM OF TONSIL, UNSPECIFIED
2 weeks ago ANEMIA, UNSPECIFIED NEW MEDICATIONS
1 day ago Cefdinir Capsule 300 MG
1 week ago Folic Acid Tablet 1 MG
1 week ago Apixaban Tablet 2.5 MG
2 weeks ago Senna Tablet 8.6 MG
2 weeks ago Prochlorperazine Maleate Tablet 10 MG
View additional new medications in E.H.R.

RECENT ORDERS
10/28/2020 STAT CXR.
10/26/2020 Stat Cjest X ray 2 views.
10/16/2020 LCS - Diet HIGHLIGHTS 810
1. Low O2 saturation of 85.0 recorded on 10/28/2020 at 22:47.
2. Maximum recorded pulse 115.0 on 10/28/2020 at 22:47.
3. 2 Diagnostic Orders in last 14 days. Last Order: "STAT CXR" on 10/28/2020 at 22:47.
4. Diagnosis of D649: ANEMIA, UNSPECIFIED recorded on 10/15/2020.

LABS & ALERT SUMMARY 806
No labs or alerts recorded in the last 30 days

RECENT PROGRESS NOTES 814

*10/28/2020 at 02:18 PM (Today) – Daily Skilled Note*
Edema present: has edema in the following extremities: Rue Non-pitting. Has moist. Non-productive cough. SOB while lying flat. Poor appetite or overeating

*10/28/2020 at 02:12 PM (Today) – COVID Monitoring*
Has moist. Non-productive cough. Cough remains unchanged.

*10/28/2020 at 06:49 AM (Today) – Daily Skilled Note*
Has moist. Non-productive cough.

*10/27/2020 at 03:28 PM (Yesterday) – Daily Skilled Note*
Resident is confused. Edema present: Has edema in the following extremities: RUE Non-pitting. Has moist, non-productive cough. SOB at rest. SOB while lying flat. Poor appetite or overeating. Resident is confused able to make needs known

SYSTEMS AND METHODS FOR REDUCING PATIENT READMISSION TO ACUTE CARE FACILITIES

RELATED APPLICATIONS

This application claims priority from U.S. Provisional Application Ser. No. 62/969,593, filed Feb. 3, 2020 and from U.S. Provisional Application Ser. No. 63/069,674, filed Aug. 24, 2020, which are incorporated by reference herein for all purposes.

TECHNICAL FIELD

The disclosed embodiments relate generally to risk identification and reduction of patient re-admittance to an acute care facility.

BACKGROUND

Patients discharged from an acute care facility, such as an emergency room or hospital, and placed in a post-acute care facility, such as a nursing or rehabilitation home, are at risk of being readmitted to the acute care facility. This is especially true for older patients and patients with more or complex medical issues. At times, the initial reason for going to the acute care facility may result in a number of undiagnosed or unidentified conditions that worsen after the patient is discharged. These undiagnosed or unidentified conditions can cause serious harm to a patient and force him or her to be returned to an acute care facility. Similarly, patients can be treated for one condition while left untreated for another that was not readily known. As such, improving the ability of post-acute care facilities to identify the patients most at risk for returning to the acute care facility improves the chances for patients to make a full recovery. However, determining which patients are most likely to be readmitted to an acute care facility is not as simple as examining the patients' medical history, as there are numerous unpredictable reasons why some patients are readmitted, and others not.

As such, a need exists for identifying patients with the highest likelihood of readmission to an acute care facility so that special care can be given to those patients.

SUMMARY

A system generates a report that ranks patients at risk for readmission to an acute care facility from a post-acute care facility. In some embodiments, the system receives, from the post-acute care facility, patient data for a plurality of patients. In some embodiments, the system inputs the patient data for the plurality of patients into a risk machine-learning system that was previously trained using historical patient data and data reflecting any readmissions from one or more post-acute care facilities to one or more acute care facilities. In some embodiments, the system determines, by the risk machine-learning system, a risk score for each patient of the plurality of patients based on each patient's patient data. Each risk score represents risk of a respective patient being readmitted to an acute care facility from the post-acute care facility. In some embodiments, the system generates, for display, the report. In some embodiments, the report includes a list of at least a subset of patients from the plurality of patients. In some embodiments, the list is further ranked from the patient with the highest risk of readmission to the patient with the lowest risk of readmission.

The methods and systems described herein identify and report the risks for a patient of a post-acute care facility to be readmitted to an acute care facility. In some embodiments, the reports are generated using historical and current data for the patients and provided to medical practitioners (e.g., physicians or nurses). In some embodiments, the historical data is used to generate machine-learning systems that are able to identify risks, rank the risks, and provide human readable explanations for the risks. In some embodiments, the generated machine-learning systems use current patient data to generate and provide the reports to the medical practitioners. In some embodiments, the provided reports allow for medical practitioners to focus on the patient with the highest risk of being readmitted to an acute care facility. In some embodiments, the reports further allow medical practitioners to efficiently input notes, diagnosis, or actions taken into the report, via an electronic device. In some embodiments, input received at the report by the medical practitioners is used as feedback to update the machine-learning systems, future reports, or the rankings of the patients. In some embodiments, the method includes identifying the patients risks and presenting the information into a report for medical practitioners to use reducing the amount of data required by providing a centralized repository for monitoring patients. Further, the ability to monitor patients and their respective risk of being readmitted to an acute care facility enables medical practitioners to provide better and more focused treatment to patients at higher risk of readmission, to help them make a full recovery.

In accordance with some embodiments, a method is performed at a computer (e.g., associated with a media content provider) having one or more processors and memory storing instructions for execution by the one or more processors. In some embodiments, the method includes receiving, from a post-acute care facility, patient data for a plurality of patients. In some embodiments, the method includes inputting the patient data for the plurality of patients into a risk machine-learning system that was previously trained using historical patient data and data reflecting any readmissions from one or more post-acute care facilities to one or more acute care facilities. In some embodiments, the method includes determining, by the risk machine-learning system, a risk score for each patient of the plurality of patients based on each patient's patient data. In some embodiments, each risk score represents risk of a respective patient being readmitted to an acute care facility from the post-acute care facility. In some embodiments, the method further includes generating, for display, a report including a list of at least a subset of patients from the plurality of patients. In some embodiments, the list is ranked from the patient with the highest risk of readmission to the patient with the lowest risk of readmission.

In some embodiments, the report includes respective patient risk scores for each of the patients in the subset of patients. In some embodiments, the method includes determining for each patient of the subset of patients one or more risk features that contributed to that patient's respective risk score. In some embodiments, the report includes one or more respective risk features for each of the subset of patients. In some embodiments, the method includes determining for each of the one or more risk features a risk feature score indicating how much that respective risk feature contributed to the risk score. In some embodiments, the report includes, for each of the respective one or more risk features, that respective risk feature's risk feature score. In some embodiments, the report includes historical risk scores for each of the subset of patients. In some embodiments, the report includes one or more conditions for each of the plurality of patients. In some embodiments, the report includes patient data for each of the plurality of patients. In some embodiments, the report includes one or more note entry fields configured to receive input from a caregiver device.

In some embodiments, the method includes receiving an input into a note entry field of the one or more note entry fields and, in response to receiving the input into the note entry field, updates the patient data. In some embodiments, the report includes one or more notification entry fields for receiving user defined notification requests, and the method includes receiving a user defined notification request into a notification entry field of the one or more notification entry fields. In response to receiving the user defined notification request, the method includes generating a notification event based on the user defined notification request. In some embodiments, a notification is provided upon occurrence of the notification event. In some embodiments, the notification event includes determining that a subsequent determined risk score for a respective patient is above a user defined risk threshold. In some embodiments, the notification event includes a user specified time. In some embodiments, the notification event includes a trigger based on an occurrence of one or more patient events.

In some embodiments, generating the report includes, preparing a separate detailed report for each patient of the subset of patients, where each detailed report for a respective patient of the subset of patients includes that respective patient's one or more risk features and corresponding one or more risk feature scores. In some embodiments, the one or more risk features that contributed to that patient's respective risk score include a respective explanation and the report includes a portion of the respective explanation for the one or more risk features. In some embodiments, the report is a spreadsheet.

In some embodiments, the acute care facility includes hospitals, emergency rooms, surgical centers, intensive care units, and urgent care centers.

In some embodiments, the patient data for a plurality of patients from the post-acute care facility includes recently collected patient data for each patient in the post-acute care facility. In some embodiments, the patient data include one or more of: a medical condition, vital statistic, date, weight, blood sugar, oxygen saturation, pain identifier, medication, note, test order, and test result. In some embodiments, the patient data include patient one or more of socio-economic data, demographic data, diet data, air quality data, social visitor data, sleep data, and movement data. In some embodiments, the patient data includes data collected from one or more patient wearable devices.

In some embodiments, the subset of patients is determined based on the plurality of patients with risk scores greater than a risk threshold. In some embodiments, the subset of patients includes a predetermined number of patients with the highest risk scores from the plurality of patients. In some embodiments, the subset of patients includes a predetermined number of patients that have been algorithmically determined.

In some embodiments, the method includes sending the report to a remote device for display. In some embodiments, the method includes displaying the report on a remote device. In some embodiments, the report is configured to be displayed on an application installed on a remote device.

In some embodiments, the method includes determining whether the risk score for a respective patient of the subset of patients is above a notification threshold and, in response to determining that the risk score is above the notification threshold, providing a notification to a medical practitioner of the post-acute care facility to follow up with the patient.

In some embodiments, the risk machine-learning system is based on at least one of unsupervised learning, supervised learning, or semi-supervised learning techniques. In some embodiments, the method includes periodically retraining the risk machine-learning system as new patient data, and data reflecting any readmissions from one or more post-acute care facilities to one or more acute care facilities, is collected. In some embodiments, the method includes, before receiving patient data for a plurality of patients, receiving historical patient data from at least one healthcare recording database. The method includes extracting training data from the historical patient data, utilizing the training data to train multiple risk machine-learning systems, selecting a risk machine-learning system of the multiple risk machine-learning systems that respectively determined risk scores above a predetermined accuracy rate, and storing the risk machine-learning system.

In some embodiments, the method includes extracting at least validation data from the historical patient data and, before storing the risk machine-learning system, inputting the validation data into the machine-learning system. In some embodiments, the method includes determining, by the risk machine-learning system, validation scores based on the validation data and, in accordance with the validation scores satisfying validation criteria, storing the machine-learning system.

In accordance with some embodiments, an electronic device (e.g., a server system, a computer system, a client device, etc.) includes one or more processors and memory storing one or more programs configured to be executed by the one or more processors. In some embodiments, the one or more programs include instructions for performing the operations of the method described above. In accordance with some embodiments, a computer-readable storage medium has stored therein instructions that, when executed by an electronic device, cause the server system to perform the operations of the method described above.

BRIEF DESCRIPTION OF THE DRAWINGS

So that the present disclosure can be understood in greater detail, a more particular description may be had by reference to the features of various embodiments, some of which are illustrated in the appended drawings. The appended drawings, however, merely illustrate pertinent features of the present disclosure and are therefore not to be considered limiting, for the description may admit to other effective features.

FIG. 5 is a report listing one or more patients, in accordance with some embodiments.

FIG. 6 is a detailed report for a respective patient, in accordance with some embodiments.

FIGS. 7A-7E are flow charts illustrating a method of generating and providing reports ranking patients at risk for readmission to an acute care facility from a post-acute care facility, in accordance with some embodiments.

FIG. 9 illustrates an additional medical practitioner report, in accordance with some embodiments.

Figure 1:
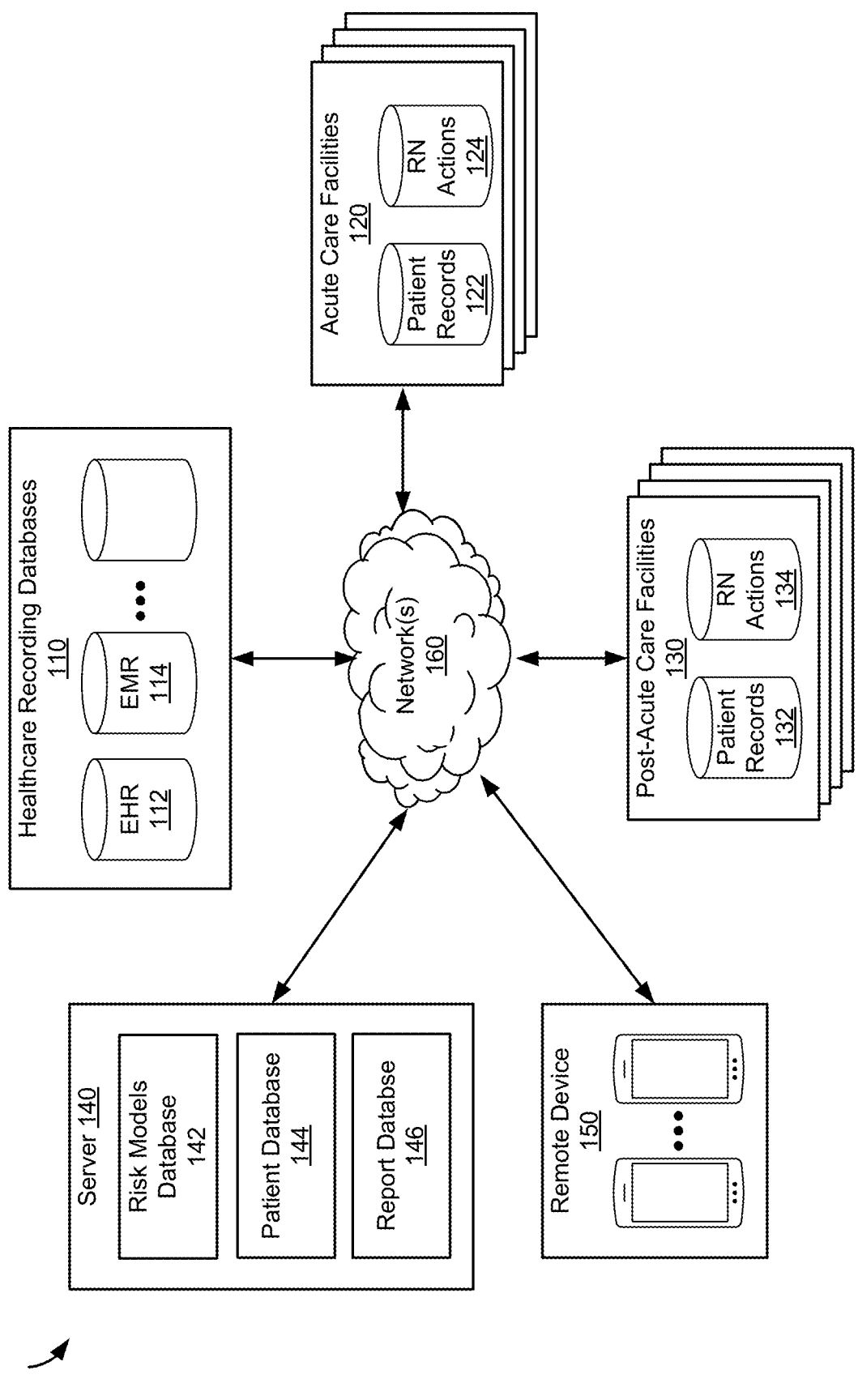
FIG. 1 is a schematic of the patient risk reporting system, in accordance with some embodiments.

In accordance with common practice, the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DETAILED DESCRIPTION

Reference will now be made to embodiments, examples of which are illustrated in the accompanying drawings. In the following description, numerous specific details are set forth in order to provide an understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

FIG. 1 is an overview of the patient risk reporting system 100 in accordance with some embodiments. The patient risk reporting system 100 includes, one or more healthcare recording databases 110, one or more acute care facilities 120, one or more post-acute care facilities 130, a server system 140, and one or more remote devices 150. One or more networks 160 communicably couple the components of the patient risk reporting system 100. In some embodiments, the one or more networks 160 include public communication networks, private communication networks, or a combination of both public and private communication networks. For example, the one or more networks 160 can be any network (or combination of networks) such as the Internet, other wide area networks (WAN), local area networks (LAN), virtual private networks (VPN), metropolitan area networks (MAN), peer-to-peer networks, and/or ad-hoc connections.

In some embodiments, the one or more healthcare recording databases 110 include one or more databases storing current and historical healthcare history of the patients. In some embodiments, the healthcare recording databases 110 are centralized or distributed. In some embodiments, the healthcare recording databases 110 are updated on a regular basis (e.g., daily, twice a week, weekly). In some embodiments, the healthcare recording databases 110 are updated based on data provided by acute care facilities 120, post-acute care facilities 130, or the server system 140. In this way, the healthcare recording databases 110 provide a centralized repository of patient data that is kept up to date and allows for easy distribution of patient data. In some embodiments, the healthcare recording databases 110 include Electronic health records (EHRs 112), Electronic medical records (EMRs 114), and/or other similar record keeping services. In some embodiments, the healthcare recording databases 110 are repositories of patient data and/or data that could affect a patient's health (e.g., air pollution, excessive heat, etc.).

In some embodiments, the healthcare recording databases 110 include data relating to medical history, medical conditions, medical diagnosis, medication and allergies, immunization status, laboratory tests ordered, laboratory test results, radiology images, vital signs, notes taken during treatment (e.g., notes from a physician, therapist, nurse, and/or other medical practitioner), free form progress notes, diet information, and other patient assessment data. In some embodiments, the healthcare recording databases 110 include patient demographic information, personal statistics (e.g., age, weight, etc.), social visitor data, billing information, socio-economic information, and other patient specific data. In some embodiments, the healthcare recording databases 110 include patient data collected via wearable devices. For instance, wearable devices, such as smartwatches; fitness tracker, mobile devices; pedometers; etc., may collect sleep data, movement data, heart rate, stress levels, etc. that are stored in healthcare recording databases 110.

In some embodiments, the healthcare recording databases 110 include environmental data such as weather, air quality, water quality, pollution, etc. In some embodiments, healthcare recording databases 110 include data received from other external systems or sources. For example, the healthcare recording databases 110 may include data from one or more agencies (e.g., the Centers for Disease Control and Prevention (CDC), Environmental Protection Agency (EPA), Food and Drug Administration (FDA), fire departments, or other agencies), local government, media outlets, internet sources, etc. that can be relevant in determining a patients' risk at a particular point in time. For instance, unusual air pollution due to fire could be provided by a fire department, viruses spread by food could be provided by a government agency, natural or man-made hazards (e.g. radiation) could be communicated by media outlets, etc. In some embodiments, the healthcare recording databases 110 include data that reflects any readmissions of a patient from one or more post-acute care facilities to one or more acute care facilities.

In some embodiments, the healthcare recording databases 110 provide patient data (e.g., historical or current) to server system 140 for training a machine-learning system and/or determining multiple patients' risks for being readmitted to an acute cate facility, as discussed below. In some embodiments, the healthcare recording databases 110 provides data to the server system 140 periodically (e.g., twice a day, daily, weekly, etc.), which is used to prepare risk reports as discussed below.

In some embodiments, the one or more acute care facilities 120 include emergency rooms, surgical centers, intensive care units, detoxification units, neonatal intensive care units (NICU), emergency psychiatric services, hospitals and hospital emergency departments, ambulatory surgery centers, urgent care centers, or other short-term stay facilities. Acute care facilities 120 provide care during which a patient is treated for sever injury or illness, trauma, urgent medical condition, or during recovery from surgery. Acute care may require a patient to stay at a facility; however, patients in acute care facilities 120 are generally discharged to post-acute care facilities 130 to complete their recovery as soon as they are deemed healthy and stable. In some embodiments, acute care facilities 120 collect patient data for one or more patients including demographics, medical history, medications and allergies, immunization status, diagnosis, laboratory test results, radiology images, vital signs, personal statistics (e.g., age, weight, etc.), and billing information (e.g., patient records 122). In some embodiments, the acute care facilities 120 collect actions and recommendations made by medical professionals (e.g., physicians, registered nurses (RN)s, etc.) (e.g., RN actions 124). In some embodiments, the acute care facilities 120 collect patient data as described above with respect to the healthcare recording databases 110. In some embodiments, the acute care facilities 120 provide their collected data to healthcare recording databases 110, server 140, and/or remote devices 150 via networks 160.

In some embodiments, the one or more post-acute care facilities 130 include nursing homes, dialysis centers, physician offices, rehabilitation facilities, psychiatric institutions. Post-acute care facilities 130 provide continued medical treatment to patients discharged from an acute care facility 120. Post-acute care facilities 130 emphasize recovery, recuperation, rehabilitation, and symptom management. For example, a patient recovering from a stroke often requires rehabilitative therapies to help them fully recover or prevent them from returning to an acute care facility 120. Post-acute care facility 130 services range from intensive short-term treatment to long-term care. As such, the goal of post-acute care facilities 130 is to ensure that patients do not return to acute care facilities. Accordingly, it is important to identify at-risk patients at a post-acute care facility 130 early on and to take the appropriate measures to prevent the patients from being readmitted to an acute care facility 120.

In some embodiments, the post-acute care facilities 130 collect patient data for one or more patients as described above with respect to acute care facilities 120. The patient data collected at the post-acute care facilities 130 is collected, e.g., during the continuous treatment of the patient while at the post-acute care facility 130. As such, in some embodiments, the patient data collected at the post-acute care facilities is more up to date with a patient's current condition (e.g., after discharged from the acute care facility 120) (e.g., patient records 132). In some embodiments, the patient data collected at the post-acute care facilities 130 also includes current diagnosis, recommendations, and actions made by medical professionals (e.g., physicians, registered nurses (RN)s, etc.) in real-time (e.g., at the time input is collected) (e.g., RN actions 134). In some embodiments, the post-acute care facilities 130 collect patient data as described above with respect to the healthcare recording databases 110. In some embodiments, the post-acute care facilities 130 provide their collected data to healthcare recording databases 110, server 140, and/or remote devices 150 via networks 160.

In some embodiments, server system 140 includes a risk models database 142, a patient database 144, and a report database 146. In some embodiments, server system 140 is communicatively connected to the one or more healthcare recording databases 110, acute care facilities 120, post-acute care facilities 130, and/or remote devices 150. In some embodiments, the server system 140 is configured to receive historical patient data and/or current patient data to train one or more risk machine-learning systems or models (hereinafter "risk models") or to determine a patients' risk for being readmitted to an acute care facility 120 from a post-acute care facility 130. The historical patient data and/or current patient data can be received from healthcare recording databases 110, acute care facilities 120, post-acute care facilities 130, and/or remote devices 150 and stored in the patient database 144. In some embodiments, the trained risk models are stored in risk models database 142. The server system 140 generates and provides one or more reports to the post-acute care facilities 130 and/or their associated remote devices 150 such that medical practitioners at the post-acute care facilities 130 can take appropriate precautions to prevent at-risk patients form being readmitted to an acute care facility 120. In some embodiments, the one or more reports are generated by applying one or more risk models. In some embodiments, the report is configured to be displayed locally at the post-acute care facilities 130 or to be displayed remote device 150 associated with the post-acute care facilities 130. In some embodiments, the generated reports are stored in report database 146. The specific operations and functions of server 140 are discussed below.

In some embodiments, remote devices 150 are associated with one or more healthcare recording databases 110, acute care facilities 120, post-acute care facilities 130, and/or server 140. In some embodiments, a remote device 150 is a personal computer, mobile electronic device, wearable computing device, laptop computer, tablet computer, mobile phone, feature phone, smart phone, or any other electronic device capable of displaying and/inputting content. Remote device 150 includes one or more programs or applications for displaying information provided by the healthcare recording databases 110, acute care facilities 120, post-acute care facilities 130, and/or server 140. In some embodiments, the Remote device 150 includes one or more inputs and/outputs for interacting with the information provided. For example, remote device can include a display, a keyboard a touch screen, a mouse, a microphone, audio output, and/or other devices.

Figure 2:
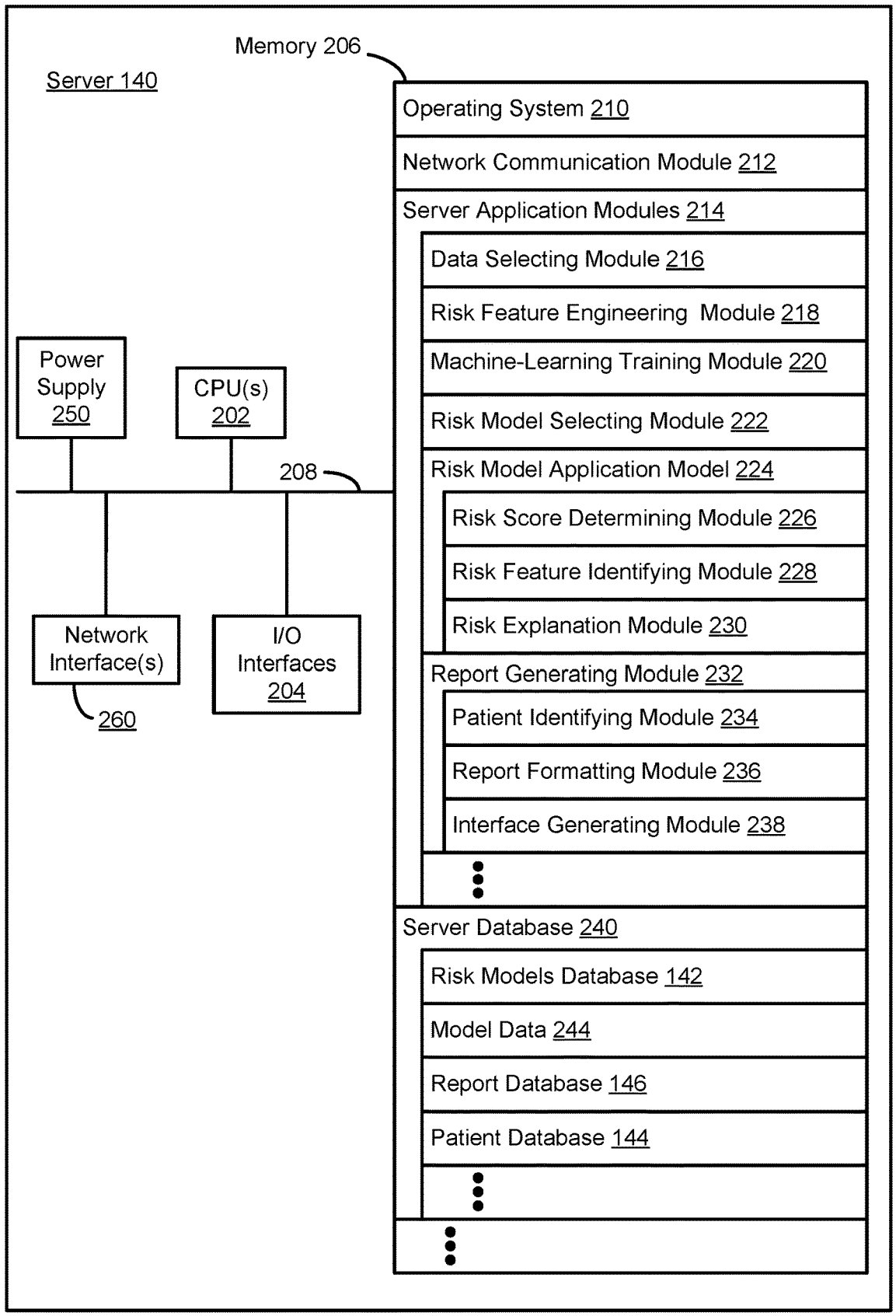
FIG. 2 is a block diagram illustrating a server system, in accordance with some embodiments.

FIG. 2 is a block diagram illustrating a server system 140 in accordance with some embodiments. The server system 140 typically includes one or more central processing units/cores (CPUs) 202, one or more network interfaces 260, memory 206, a power supply 250, and one or more communication buses 208 for interconnecting these components. The communication buses 208 optionally include circuitry (sometimes called a chipset) that interconnects and controls communications between system components. The server system 140 includes I/O interfaces 204. In some embodiments, the I/O interfaces 204 include a keyboard, mouse, a microphone, and/or track pad. Alternatively, or in addition, in some embodiments, the I/O interfaces 204 includes a display device that includes a touch-sensitive surface, in which case the display device is a touch-sensitive display. "User input," as described herein, may refer to a contact detected with a touch-sensitive display and/or an input by an I/O interface 204. In some embodiments, the I/O interfaces 204 include a display, speaker, or other devices for providing information (e.g. content, graphs, tables, data, etc.) to a user.

In some embodiments, the one or more network interfaces 260 include wireless and/or wired interfaces for receiving data from and/or transmitting data to one or more healthcare recording databases 110, acute care facilities 120, post-acute care facilities 130, and/or other devices or systems. In some embodiments, data communications are carried out using any of a variety of custom or standard wireless protocols (e.g., NFC, RFID, IEEE 802.15.4, Wi-Fi, ZigBee, 6LoWPAN, Thread, Z-Wave, Bluetooth, ISA100.11a, WirelessHART, MiWi, etc.). Furthermore, in some embodiments, data communications are carried out using any of a variety of custom or standard wired protocols (e.g., USB, Firewire, Ethernet, etc.).

Memory 206 includes high-speed random access memory, such as DRAM, SRAM, DDR RAM, or other random access solid-state memory devices; and may include non-volatile memory, such as one or more magnetic disk storage devices, optical disk storage devices, flash memory devices, or other non-volatile solid-state storage devices. Memory 206, optionally, includes one or more storage devices remotely located from one or more CPUs 202. Memory 206, or, alternatively, the non-volatile solid-state memory device(s) within memory 206, includes a non-transitory computer-readable storage medium. In some embodiments, memory 206, or the non-transitory computer-readable storage medium of memory 206, stores the following programs, modules and data structures, or a subset or superset thereof:

- an operating system 210 that includes procedures for handling various basic system services and for performing hardware-dependent tasks;
- a network communication module 212 that is used for connecting the media content server 108 to other computing devices via one or more network interfaces 260 (wired or wireless) connected to one or more networks 160;
- one or more server application modules 214 for performing various functions with respect to utilizing machine-learning systems and generating reports identifying patients' risk for returning to an acute care facility 120, the server application modules 214 including, but not limited to, one or more of:
  - a data selecting module 216 for determining and storing training data sets, validation data sets, test data sets, and current patient data sets from the patient data received from the healthcare recording databases 110, acute care facilities 120, and/or post-acute care facilities 130 stored in patient database 144;
  - a risk feature engineering module 218 for determining one or more risk features that structure the data sets determined by the data selecting module 216, and risk features that can be used as inputs into a trained risk model;
  - a machine-learning training module 220 for training, tuning, and testing one or more risk models using various machine-learning techniques, patient data sets received from the data selecting module 216, and one or more risk features received from the risk feature engineering module 218;
  - an (optional) risk model selecting module 222 for selecting one or more machine-learning systems or models to analyzing the patient data sets determined by the data selecting module 216;
  - a risk model application module 224 for applying one or more risk models trained by the machine-learning training module 220 to the patient data sets determined by the data selecting module 216, the risk model application module 224 including, but not limited to, one or more of:
    - a risk score determining module 226 for determining risk scores for each patient in the patient data received from the data selecting module 216,
    - a risk feature identifying module 228 for determining and identifying one or more risk features that contribute to the risk score of a patient determined by the ML risk score determining module 226, and
    - a risk explanation module 230 for determining and generating one or more explanations for each risk scores and each identified risk feature of a patient;
  - a report generating module 232 for generating one or more reports for display of the determined risk scores for patients of a post-acute facility 130, the report generating module 232 including, but not limited to, one or more of:
    - a patient identifying module 234 for identifying and ranking one or more patients to be included in a generated report,
    - a report formatting module 236 for determining the format of the generated reports, and
    - an interface generating module 238 for determining and generating one or more interfaces for enabling an end user to input information into the report, establish one or more conditions, and/or reporting between user in the post-acute care facility 130 or healthcare recording databases 110; and
  - a server database 240 for storing and accessing patient data from the healthcare recording databases 110, acute care facilities 120, and/or post-acute care facilities 130, the server database 240 including, but not limited to, one or more of:
    - a risk models database 142 for storing and accessing one or more risk models that were previously trained, validated, and tested by the machine-learning training module 220;
    - Model data 244 for storing and accessing identified training data, validation data, test data, and current patient data for training or applying one or more risk models;
    - a report database 146 for storing and accessing one or more generated reports provided to the post-acute care facilities 130 and using the data in the generated reports for additional data in subsequently generated reports; and
    - patient database 144 for storing and accessing raw healthcare and patient data received from healthcare recording databases 110, acute care facilities 120, and/or post-acute care facilities 130.

In some embodiments, the server 140 includes web or Hypertext Transfer Protocol (HTTP) servers, File Transfer Protocol (FTP) servers, as well as web pages and applications implemented using Common Gateway Interface (CGI) script, PHP Hyper-text Preprocessor (PHP), Active Server Pages (ASP), Hyper Text Markup Language (HTML), Extensible Markup Language (XML), Java, JavaScript, Asynchronous JavaScript and XML (AJAX), XHP, Javelin, Wireless Universal Resource File (WURFL), and the like.

Each of the above identified modules stored in memory 206 corresponds to a set of instructions for performing a function described herein. The above identified modules or programs (i.e., sets of instructions) need not be implemented as separate software programs, procedures, or modules, and thus various subsets of these modules may be combined or otherwise re-arranged in various embodiments. In some embodiments, memory 206 optionally store a subset or superset of the respective modules and data structures identified above. Furthermore, memory 206 optionally store additional modules and data structures not described above. In some embodiments, modules described above with regard to memory 206 are stored at remote device 150 or non-transitory computer system (and vice-versa). For example, the report generating module 232 may be stored at the server 140 in memory 206 and/or stored at the remote device 150.

Although FIG. 2 illustrates the server 140 in accordance with some embodiments, FIG. 2 is intended as a functional description of the various features that may be present in one or more media content servers than as a structural schematic of the embodiments described herein. In practice, and as recognized by those of ordinary skill in the art, items shown separately could be combined and some items could be separated. For example, some items shown separately in FIG. 2 could be implemented on single servers and single items could be implemented by one or more servers. The actual number of servers used to implement the server 140, and how features are allocated among them, will vary from one embodiment to another and, optionally, depends in part on the amount of data traffic that the server system handles during peak usage periods as well as during average usage periods.

Figure 3:
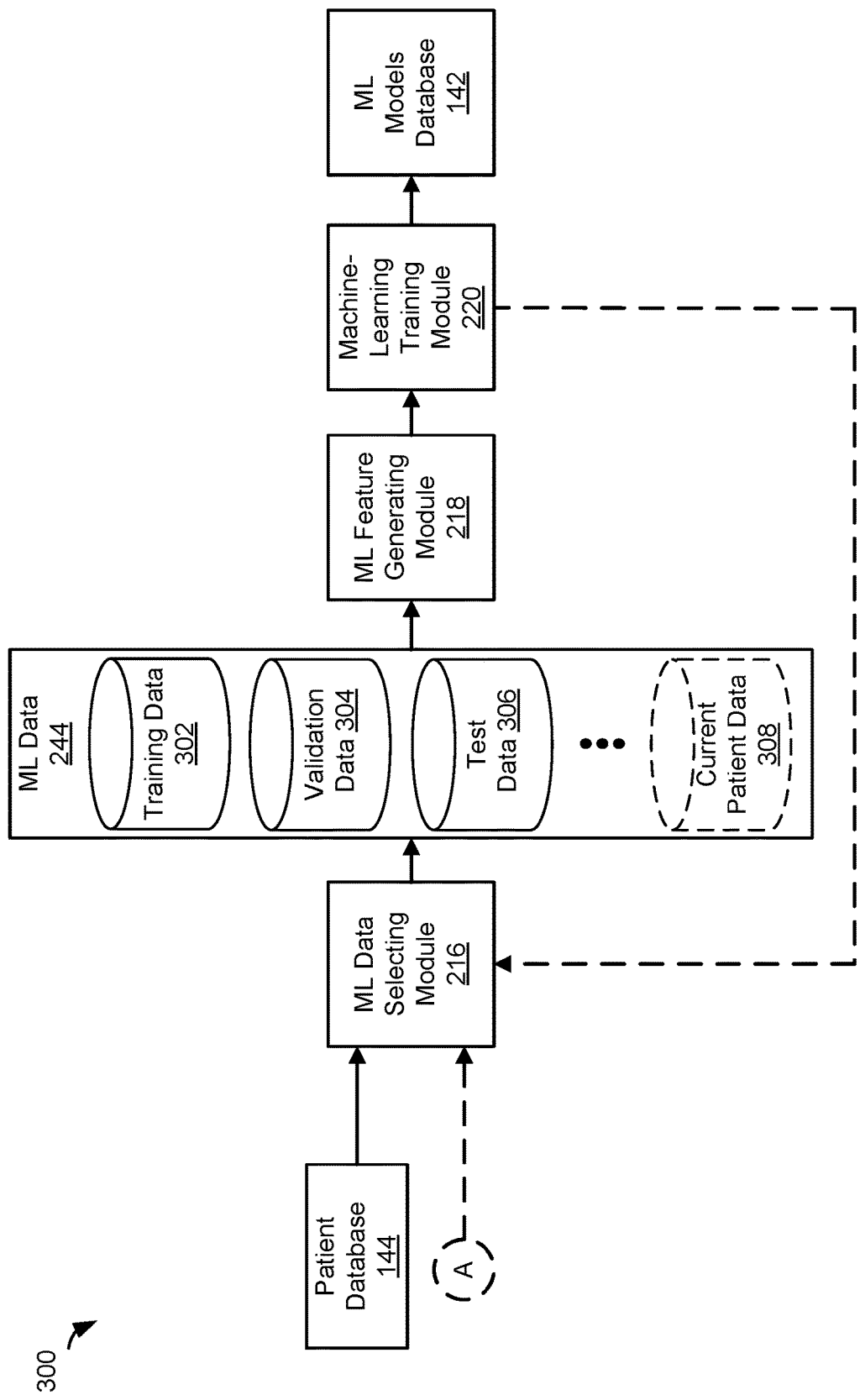
FIG. 3 is a block diagram illustrating training of a risk machine-learning system or model, in accordance with some embodiments.

FIG. 3 illustrates training of a risk model in accordance with some embodiments. In some embodiments, machine-learning training system 300, via server 140, receives patient data from one or more healthcare recording databases 110, acute care facilities 120, and/or post-acute care facilities 130, and the patient data is stored in a patient database 144. The patient data is described above in relation to FIG. 1. The machine-learning training system 300 uses a data selecting module 216 to select different subsets of the patient data in the patient database 144 (e.g., provided by the healthcare recording databases 110, acute care facilities 120, and/or post-acute care facilities 130). In some embodiments, the data selecting module 216 identifies historical patient data to train a risk model. In some embodiments, the data selecting module 216 determines a predetermined time period and/or a predetermined number of patients to include in the historical patient data. The predetermined time period for the historical patient data can span 1 year, 3 years, 5 years, 10 years, etc.; or any other time period defined by a user. The predetermined number of patients for the historical patient data can include hundreds, thousands, millions, etc. of patients; or a number defined by the user.

Alternatively or additionally, in some embodiments, the data selecting module 216 receives feedback from the machine-learning training module 220 that is used to adjust the historical patient data (e.g., adjust the number of patients and/or time period in which patients are included). In some embodiments, the data selecting module 216 adjusts the predetermined time period and/or the predetermined number of patients for the historical patient data such that a trained risk model meets a minimum accuracy rate. For instance, a trained risk model, as explained in detail below, may have an accuracy rate below the minimum accuracy rate and the machine-learning training system 300 can adjusts the predetermined time period and/or the predetermined number of patients for the historical patient data to retrain a risk model with an accurate rate above the minimum accuracy rate. The accuracy rate for a trained risk model is determined by machine-learning training module 220 as discussed below.

The data selecting module 216 selects the historical patient data to train a risk model that covers different illnesses, diseases, sicknesses, conditions, and/or other potential ailments as well as across different locations, patients, age groups, etc. Alternatively or additionally, in some embodiments, the data selecting module 216 selects the historical patient data to train a machine-learning model for on one or more particular illnesses, diseases, sicknesses, conditions, and/or other potential ailments. In this way, one or more risk models can be specialized for one or more post-acute care facilities, patients, illnesses, diseases, sicknesses, conditions and/or other potential ailments. Similarly, in some embodiments, the data selecting module 216 selects the historical patient data based on geographic location. In some embodiments, the data selecting module 216 can combine different portions of the historical patient data to train a model (e.g. patient data described above in relation to FIG. 1). For example, the data selecting module 216 can combine historical weather patterns with the different medical conditions and illnesses. The data selecting module 216 can select historical patient data from the healthcare recording databases 110 in any number of different ways to train one or more risk models that can operate universally (e.g. across different locations and different situations) or that are specialized (e.g. for specific locations, environmental conditions, hazards, patients, and/or medical conditions).

In some embodiments, the data selecting module 216 processes the patient data to clean, standardizes, sanitize, samples, normalizes, and/or organize the collected data in the patient database 144. In some embodiments, the data selecting module 216 performs optical character recognition (OCR) on different notes (handwritten or typed) to determine information that can be used to train a risk model or to make risk determinations. In some embodiments, the data selecting module 216 does not process the patient data and uses the raw information as stored in the patient database 144.

In some embodiments, the data selecting module 216 determines one or more subsets of the historical patient data to store to model data 244 of the server database 240. In some embodiments, the data selecting module 216 selects training data 302, validation data 304, and test data 306 from the historical patient data. The training data 302, validation data 304, and test data 306 is stored to the model data 244 of the server database 240 and is used to train one or more risk models. The training data 302 is a subset of the model data 244 that is used by the machine-learning training module 220 to train one or more risk models. The validation data 304 is a subset of the model data 244 that is held back from training the one or more risk models. The validation data 304 is used by the machine-learning training module 220 to evaluate the risk models' performance (e.g. accuracy rate) while tuning the risk models' hyperparameters (e.g., a risk models' hidden units). Because validation data 304 is used to evaluate the risk models' performance while tuning the risk models' hyperparameters, the validation data 304 becomes biased over time. An unbiased set of data, the test data 306, is used by the machine-learning training module 220 to evaluate the performance of fully trained risk models. The test data 306 is a subset of the model data 244 that is held back from training the one or more risk models and is distinct from the training data 302 and validation data 304. The training, validation, and testing of the one or more risk models is discussed below in reference to the machine-learning training module 220. In some embodiments, the data selecting module 216 determines current patient data 308, which is discussed in more detail in relation to FIG. 4.

In some embodiments, the model data 244 is provided to the feature engineering module 218 to determine one or more risk features from the model data 244. Risk features are the transformation of patient data (e.g., in the training 302, validation 304, and test 306 data) from a raw state (e.g., unstructured) to a state suitable (e.g. structured) for generating one or more risk models. In some embodiments, the risk features are a representation of an underlying problem that a risk model trained to solve. For example, the risk features can help identify one or more risks that can cause a patient discharged from an acute care facility 120 to be readmitted to the acute care facility 120 (e.g., for either the same or different medical reasons). Risk features can also help improve the accuracy of risk model when processing unseen data by describing and/or providing structure to the patient data, in this case the training 302, validation 304, and test 306 data in model data 244. In some embodiments, the risk feature engineering module 218 transforms each element of the patient data in the model data 244 (e.g., patient data described above in relation to FIG. 1) into one or more risk features. In some embodiments, the feature engineering module 218 transforms a subset of and/or a combination of the patient data elements in the model data 244 into one or more risk features.

As an example, risk features can be generated for each medication that a patient is taking or has taken, risk features can be generated for the number of dosages that a patient has been given or refused to take. In some embodiments, the risk features can define minimums and maximums for occurrences in the patient data. For example, risk features can be created for a maximum and minimum daily blood pressure. In some embodiments, the risk features could be combinations of related or unrelated factors. For example, in some embodiments, risk features can be generated for adverse effects caused by combining two medications, risk features can be generated for the effect of air pollution and/or weather conditions to asthma and or other conditions. In some embodiments, risk features can be generated to include advisory notices or other potential warnings that may affect a patient's health. In some embodiments, the or more risk features are generated for data reflecting any readmissions of a patient from one or more post-acute care facilities to one or more acute care facilities. In short, any data element or different combination of data elements in the patient data described in relation to FIG. 1 and received by server 140 can be used to determine one or more risk features. The one or more generated features are further used to define the inputs for one or more trained risk models as discussed below.

In some embodiments, the one or more risk features generated by the risk feature engineering module 218 are provided to the machine-learning training module 220 to define and/or structure the inputs of a trained risk model. In some embodiments, the machine-learning training module 220 applies different techniques (e.g., algorithms) to train one or more risk models that will make determinations (e.g., risk score evaluations or predictions) based on patient data. In some embodiments, a trained risk model uses the generated risk features as inputs to a trained risk model. In some embodiments, after training a risk mode (discussed below), the machine-learning training module 220 tunes and tests the trained risk model. In some embodiments, the machine-learning training module 220 trains one or more risk models based on unsupervised learning, supervised learning, and/or semi-supervised learning.

Turning to the training risk model training process, as described above, the historical patient data is divided, by the data selecting module 216, into at least three subsets of model data 244. The at least three subsets of model data 244, training data 302; validation data 304; and test data 306, are used by the machine-learning training module 220 to generate the one or more risk models.

In some embodiments, the machine-learning training module 220 uses the training data 302 to determine one or more parameters and hyperparameters for an risk model. A parameter is a variable that is internal to the risk model and whose value can be estimated from the training data 302. A parameter is the part of risk model that is learned from the historical training data 302 and not set manually by a user. One or more parameters are required by a risk model to make determinations (e.g., risk score evaluations or predictions) and are saved as part of the risk model. Further, the parameters define the performance (e.g., accuracy) of the trained risk model. In short, the machine-learning training module 220 generates a risk model with one or more parameters that are determined by the training data 302 provided. The performance of the risk mode is dependent on the parameters.

Hypermeters, on the other hand, are external to the risk model and has a value that cannot be estimated from the training data 302. In some embodiments, one or more hyperparameter are used in risk model training processes to help estimate the one or more of the parameters. In some embodiments, the one or more hyperparameters are specified by the user (e.g., via the I/O interfaces 204 or network interfaces 260). In some embodiments, the one or more hyperparameters are set using heuristics. In some embodiments, the one or more hyperparameters are tuned for a risk model and help identify one or more parameters that cannot be estimated from the training data 302, but contribute to the performance of the risk model in a significant way. As discussed below, the machine-learning training module 220 uses the validation data 304 to determine (e.g., tune) one or more hyperparameters for a risk model.

In some embodiments, the machine-learning training module 220 generates an risk model that includes one or more initial hyperparameters that are configurable (e.g., can be modified by a user as described above). In some embodiments, the validation data 304 is input into the trained risk model and one or more adjustments are made to the hyperparameters. The one or more adjustments to the hyperparameters are used to improve the performance of the risk model. As explained above, the validation data 304 is a portion of the historical patient data that is held back in the initial training of a risk model, but becomes biased as the risk model is tuned (e.g., adjustments to the one or more hyperparameters). In some embodiments, one or more risk models can have the same or different hyperparameters. Alternatively or additionally, in some embodiments, distinct ML models can have the same or different hyperparameters.

In some embodiments, after the risk model is tuned, the machine-learning training module 220 uses the test data 306 to determine the performance of the risk model. As mentioned above, the test data 306 is a portion of the historical patient data that is unbiased (e.g., not used in the training or tuning process) and used to provide an accurate measurement of the risk models performance. In some embodiments, the machine-learning training module 220 receives the test data 306 and determines one or more risk scores. The performance of the risk model is based on the accuracy of the risk scores for one or more patients in the test data. In some embodiments, risk models with a performance (e.g., accuracy rate) at or above a predetermined accuracy rate (e.g., at least 75 percent accurate) are stored to the risk models database 142. Alternatively or additionally, in some embodiments, risk models with a performance below the predetermined accuracy rate are not stored to the risk models database 142. In some embodiment, the risk models are stored in the risk model database and include the parameters, hyperparameters, the generated features, and/or other model weights for using the machine-learning model on new patient data as discussed in relation to FIG. 4.

In some embodiments, the machine-learning training module 220 provides feedback to the data selecting module 216 about the stored and/or discarded machine-learning models. In some embodiments, the feedback provided by the machine-learning training module 220 is used to adjust the model data 244 and/or adjust the one or more features (e.g., generated by the feature engineering module 218) for one or more risk models. In some embodiments, the model data 244 is adjusted by increasing or decreasing the number of patients and/or the predetermined time period observed. In some embodiments, the one or more features are adjusted by selecting new features, using different combination of features, using more or less features, modifying the previously selected features, and/or other adjustments. In this way, both stored and discarded risk models can be improved with the information learned over the training process and a repository of different risk models utilizing different machine-learning techniques or trained for different purposes (e.g., specialized risk models) can be established.

Figure 4:
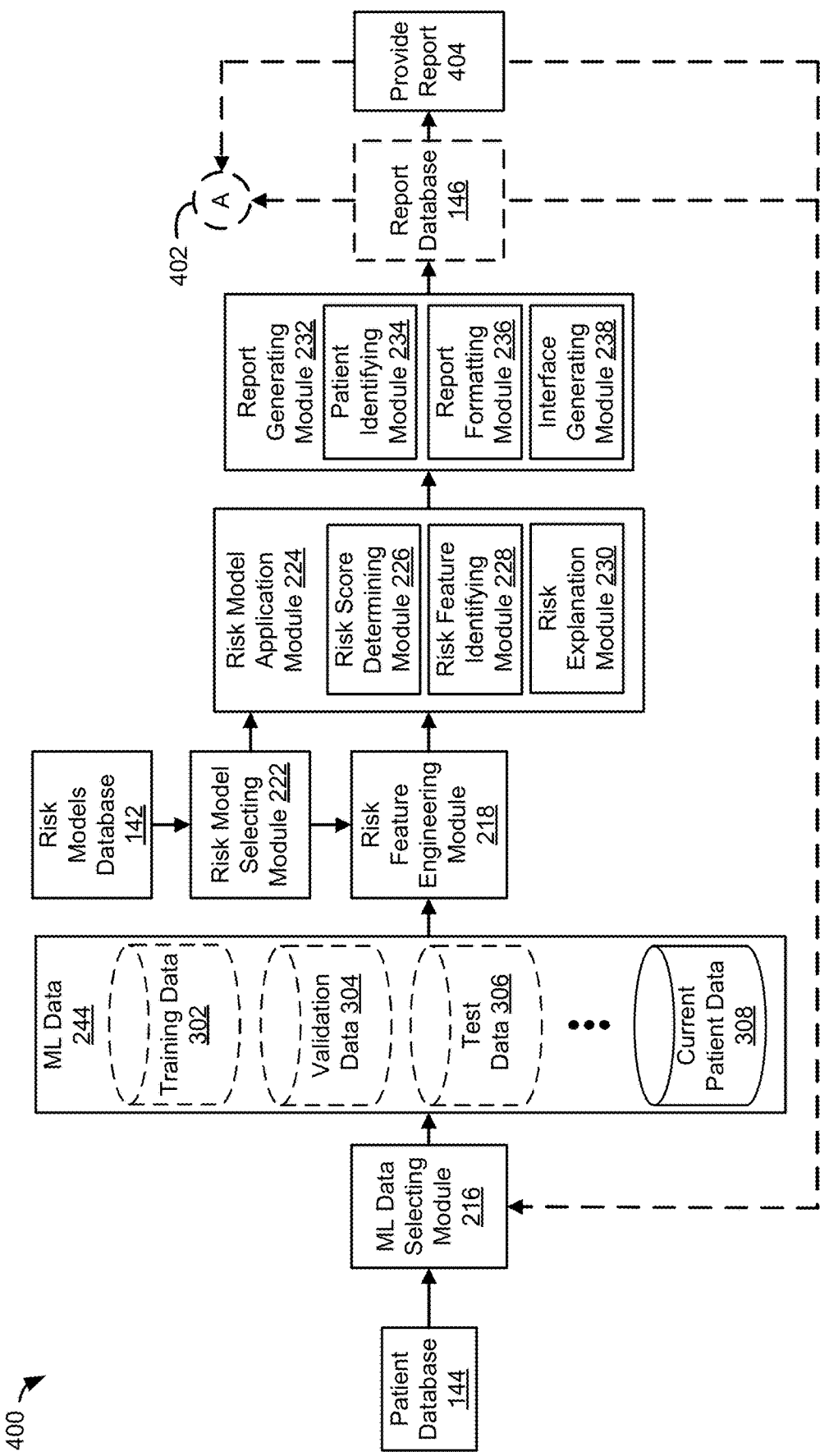
FIG. 4 is a block diagram illustrating using one or more risk machine-learning systems or models for providing a patient report, in accordance with some embodiments.
Figure 7A:
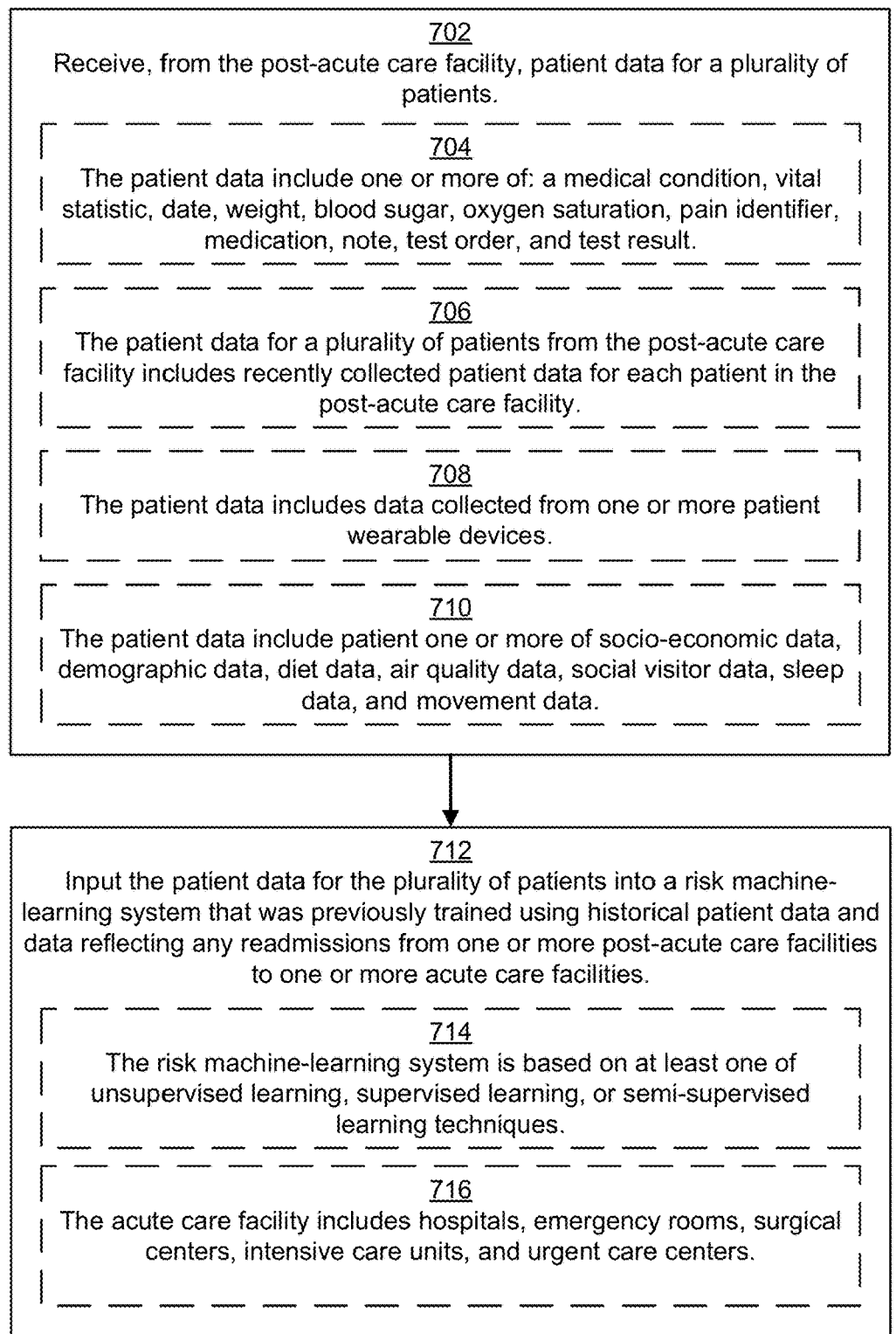

FIG. 4 illustrates using one or more risk models for providing a patient report, in accordance with some embodiments. In some embodiments, report generating system 400 uses patient data in a patient database 144 (e.g., patient data received from one or more healthcare recording databases 110, acute care facilities 120, and/or post-acute care facilities 130). Examples of the patient data are described above in relation to FIG. 1. Similar to the process described in relation to FIG. 3, in some embodiments, the report generating system 400 uses the data selecting module 216 to determine a subset of the patient data in the patient database 144 to use in applying a risk model and generating a report. In some embodiments, the data selecting module 216 identifies recently collected patient data the patient database 144 to generate one or more patient reports. In some embodiments, the data selecting module 216 determines recently collected patient data for each patient at post-acute care facility 130 that is going to receive a report. Recently collected data includes data from the one or more healthcare recording databases 110, acute care facilities 120, post-acute care facilities 130, and/or remote device 150 that was collected during the course of a day, updated at the end of a day, collected after a patient is discharged from an acute care facility 120, or collected at predetermined intervals of a given day (e.g. every 2 hours, 6 hours, 12 hours, overnight, etc.). In some embodiments, the recently collected patient data can also include patient data for the current day (e.g., collected at the start of the day (12:00 AM) or intermittently throughout the day), the past two days, the past three day, or within a week.

As described above in relation to FIG. 3, the data selecting module 216 processes (e.g., performs optical character recognition (OCR), cleans, standardizes, normalizes, organizes, etc.) the recently collected patient data and stores the data to model data 244 of the server database 240. The current patient data 308 is a subset of the model data 244 that is input to one or more trained risk models (described in relation to FIG. 3). The current patient data 308 is distinct from the training data 302, validation data 304, and test data 306. In some embodiments, the current patient data 308 is updated with previously generated reports and/or with inputs to the previously generated reports by one or more medical practitioners via network 160 (discussed further below).

In some embodiments, the risk model selecting module 222 selects one or more risk models from the risk models database 142 of server database 240 to apply to the current patient data 308. In some embodiments, the risk model selecting module 222 selects a risk model with the highest accuracy rate (e.g., the risk model with the highest measured performance based on the test data 306 as described in relation to FIG. 3). In some embodiments, the risk model selecting module 222 selects a risk model for a particular post-acute care facility 130 (e.g., a customized risk model for a nursing homes, physician offices, or other post-acute care facilities identified in FIG. 1), a particular illness; sickness; disease; or conditions (e.g., strokes, heart attacks, seizures, or other medical conditions identified in FIG. 1), patient demographic, or any other attribute specific to patients and/or post-acute care facility 130.

Alternatively or additionally, in some embodiments, the risk model selecting module 222 selects a plurality of risk models to be applied to the current patient data 308. In some embodiments, the plurality of risk models are operated in parallel and the risk model that performs with the greater accuracy rate is used to generate the report. In some embodiments, the plurality of risk models are operated in parallel to eliminate conflicting or abnormal or verify results generated by one or more risk model. In some embodiments, the plurality of risk models are operated as an ensemble (e.g., sequentially or in a combination with each other). Different combinations of the risk models in the risk models database 142 can be used to generate accurate risk scores determining the causes and/or likelihood of patient being readmitted to an acute care facility 120.

In some embodiments, the risk model selecting module 222 identifies the one or more selected risk models to the risk feature generating module 218 and the risk application module 222. In some embodiments, the risk feature engineering module 218 generates one or more features specific to the selected risk model for the current patient data 308 of the model data 244. As described above in relation to FIG. 3, when one or more risk models are trained, the risk feature engineering module 218 generates one or more risk features to structure the data. The one or more risk features are provided to the risk model as it is trained to improve the performance (e.g. accuracy) of the risk models when provided with new data (e.g., providing a data structure). Similarly, the risk feature engineering module 218 generates one or more features from the current patient data 308 such that the selected risk model receives expected inputs (e.g., each patient's data is adjusted or formatted to fit the generated one or more features). In some embodiments, different risk models have different features and knowing the selected risk models reduces the processing required by the risk feature engineering module 218 by allowing the risk feature engineering module 218 to generate the specific features required for a selected risk model.

In some embodiments, the risk model application module 224 receives the one or more risk features generated by the risk feature engineering module 218 and uses the one or more risk features with the risk models selected by the risk model selecting module 222. In some embodiments, the risk score determining module 226 determines a risk score for each patient in the current patient data 308. In some embodiments, the risk score for each patient is based on each patient's data as provided in the one or more generated features. The risk score is a representation of a patient's overall risk of being readmitted to an acute care facility 130 from a post-acute care facility 130. In some embodiments, each patient's risk score is a combination of an estimated risk for each feature of the one or more generated features (as discussed below).

In some embodiments, the risk model application module 224 uses a risk feature identifying module 228 to determine the one or more risk feature that contribute to a patient's risk score. In some embodiments, each of the risk features identified to have contributed to the patient's risk score is assigned a risk feature score. The risk feature score represents a risk features contributing weight to the overall risk score determined by the risk score determining module 226. In some embodiments, a risk feature score is represented as a percentage of the risk score. In some embodiments, the risk feature scores are determined by analyzing a respective risk feature's impact on the performance of the risk model as a whole. In some embodiments, each risk feature is analyzed to determine a respective risk feature score. In some embodiments, each patients' risk score is provided with the one or more determined risk feature scores.

In some embodiments, the risk model application module 224 uses a risk explanation module 230 to generate one or more human readable explanations for the risk scores, risk features, and/or risk feature scores determined for the one or more patients. In some embodiments, the risk explanation module 230 generates an overview description of the risk score that identifies the contributing risk features for the risk score. For instance, the overview description may list the contributing risk features for a given risk score. In some embodiments, the overview description lists the contributing risk features in order from the highest contributing risk feature to the lowest contributing feature (based on risk feature scores). In some embodiments, the overview description includes a predetermined number of risk features (e.g. top five risk features).

Alternatively or additionally, in some embodiments, the risk explanation module 230 generates a detailed description for the risk score and/or risk feature score. In some embodiments, the risk explanation module 230 utilizes the patient data for a particular patient (e.g., from the current patient data 308) to provide an explanation for the risk score and/or risk feature score. For example, a patient may have been provided with two different medications that the model has determined to place a patient at risk of returning to an acute care facility 120. The risk explanation module 230 would provide both medications and their respective dosages as well as flag the information for a medical practitioner. In some embodiments, the risk explanation module 230 provides an explanation as to the interaction between two or more risk features. For instance, a medication used by a patient recovering from a heart attack may significantly increase the risk of the patient being readmitted to an acute care facility 120. The risk explanation module 230 may provide an explanation of the dependency between the two features (e.g., heart attack and medication). In some embodiments, the risk explanation module 230 uses one or more notes in the patient data to generate an explanation. In some embodiments, the risk explanation module 230 highlights one or more words or phrases that were entered in the patient data and identified as a risk feature. Any number of explanations can be generated by the risk explanation module 230 by using the data available in the current patient data 308 and the determined risk score and risk feature scores. The risk explanations generated by the risk explanation module 230 are provided the report generating module 232 to be included in the report.

In some embodiments, the report generating module 232 uses the results from the risk model application module 224 to generate one or more reports and detailed reports. In some embodiments, the reports include a list of one or more patients from the current patient data 308 and their respective risk score. Additionally or alternatively, in some embodiments, the report generating module 232 generates a detailed report, separate from the reports that list one or more patients, for each patient of the one or more patients on the report. In some embodiment, the detailed report includes the respective risk features and corresponding risk feature scores for the one or more patients. The information provided in the one or more reports and detailed reports is discussed below in relation to FIGS. 5 and 6.

In some embodiments, the patient identifying module 234 identifies a subset of the one or more patients with a risk score above a predetermined threshold (e.g., 50 percent or above). For example, patients with a determined risk score above 50 percent are placed on the generated report. Additionally or alternatively, in some embodiments, the patient identifying module 234 identifies a subset of the one or more patients that includes a predetermined number of patients with the highest risk score. For instance, in some embodiments, the generated report is configured to include a maximum number of patients (e.g., 25, 50, 100, 150, etc.) and the patients with the highest determined risk scores are included in the subset of patients. In other embodiments, the subset of patients include a predetermined number of patients that have been algorithmically determined. In some embodiments, the patient identifying module 234 ranks the patients in the subset of one or more patients. The ranked patients are listed in ascending order based on their respective risk scores. In other words, the patients in the subset of patients is ranked from the patient with the highest risk of readmission to the patient with the lowest risk of readmission (based on respective risk scores).

In some embodiments, the report generating module 232 includes a report formatting module 236 that determines the format and layout of the one or more reports or detailed reports. In some embodiments, the one or more generated reports are spreadsheets, tables, graphs, charts, plots, or other visual data distributions. In some embodiment, the report formatting module 236 determines one or more labels, rows, columns, headers, titles, legends, axis, or other characteristics for the presentation of the information. In some embodiments, the report formatting module 236 links or connects together one or more reports and or detailed reports. For instance, in some embodiment, the report formatting module 236 can link together a report that list of a plurality of patients with the respective patients detailed report (as discussed below in relation to FIGS. 5 and 6).

In some embodiments, the report generating module 232 includes an interface generating module 238 that generates one or more interfaces for a user to interact with the report or detailed report. In some embodiments, interface generating module 238 enables user input into the one or more generated reports and detailed reports to be communicated back to the one or more healthcare recording databases 110, acute care facilities 120, and/or post-acute care facilities 130 (e.g., via network 160). In some embodiments, the interface generating module 238 allows for the report or detailed report to update the patient data as input is received. In some embodiments, the patient risk score and risk feature scores are updated as input is received by the one or more reports or detailed reports. For example, a user changing the medication for a patient could raise or lower a corresponding risk score or risk feature score (e.g., lowering the ordered Diuretics from 4 to 1).

In some embodiments, the interface generating module 238 generates one or more fields in the report or detailed report that enables a user to define (e.g., set up) one or more notification requests or events. The one or more reports or detailed reports generate one or more notification events based on the user defined notification requests or events. When the event or request is triggered the report or detailed report can provide a notification to one or more medical practitioners (e.g., physicians or nurses) of a post-acute care facility 130 (e.g., via a user device associated with the post-acute care facility 130). In some embodiments, the one or more notification events or triggers include a patient's risk score rising above a user defined level, a patient's risk feature score rising above a user defined level, the occurrence of an event (e.g., patient vomited, patient blood pressure is low, etc.), a specified time (e.g., 3 PM, 6 PM, 10 PM, etc.) or any other customizable event set by the user.

In some embodiments, after the one or more reports and/or detailed reports are generated, the report generating system 400 stores the reports and detailed reports to the report database 146 of server 140. In some embodiments, the stored reports and detailed reports are used to update future reports and detailed reports generated by one or more risk models. Alternatively or additionally, in some embodiments, the stored reports and detailed reports are provided to train one or more new risk models. For instance, as shown by operation 402, the stored reports and detailed reports can be provided to the data selecting module 216 to update the training data 302, validation data 304, and the test data 306. The updated training data 302, validation data 304, and test data 306 can be used to generate new risk models or update and replace existing risk models. Similarly, the store reports and detailed reports can be provided to the data selecting module 216 to update the current patient data 308. Updating the current patient data 308 allows for updated risk scores and risk feature scores to be determined.

In some embodiments, the generated reports and detailed reports are provided 404, for display, to the post-acute care facilities 130 and/or one or more devices associated with the post-acute care facilities 130. Although not shown, in some embodiments, input received 406 to the one or more reports and detailed reports is provide to the data selecting module 216 to update the training data 302, validation data 304, test data 306, and/or the current patient data 308. The updated data can be used to update or generate new reports and detailed reports, or to create new risk models, update existing models, or replace existing risk models.

FIG. 5 illustrates a report listing one or more patients in accordance with some embodiments. In some embodiments, report 500 includes a data visualization 502 that includes one or more patients and one or more data fields. In some embodiments, the data visualization is presented as a spreadsheet, table, graph, chart, plot, or the like. In some embodiment, the one or more data fields include rows, columns, titles, legends, data points, etc. In some embodiments, the report 500 includes an indication 504 of one or more facilities that the report was generated for, the date the report was generated, and the time the report was generated. For example, FIG. 5 shows that the report 500 was "Prepared for Northbrook Oaks Facility Jan. 29, 2020 03:56 AM EST." In some embodiments, the report includes a subset of patients that is determined as described above in relation to FIG. 4. For example, as shown in FIG. 5, a subset of 15 patients is included in the report 500. In some embodiments, the one or more patients are identified by their name 506. Alternatively or additionally, in some embodiments, the one or more patients are identified by a patient identification number such that a patient's personal information is protected.

In some embodiments, each patients' risk score is displayed in report 500. Alternatively or additionally, in some embodiments, the report includes a ranking 508 of subset of patients. As described above in relation to FIG. 4, patients are ranked from those with the highest risk score to those with the lowest risk score. For example, as shown in FIG. 5, the subset of patients are ranked from rank 1 (Mr. Jones) to rank 15 (Ms. Spice). In some embodiments, the report 500 includes a patients' respective ranking or risk score for the previous day 510, if any. For example, both Mrs. Tones and Mr. Jones have only been on the report for 1 day and do not have an assigned ranking for the previous day. In some embodiments, the report includes the number of days 512 that the patient has been on the report. For example, as shown in FIG. 5, Ms. Lee has been on the report for a total of 33 while other patients have been on the report for more or less time (e.g., Mrs. Dan being on the report for 15 days and Mr. Reed being on the report for 43 days). In some embodiments, the report 500 includes one or more dates 514. In some embodiments, the one or more dates include the date that a patient was admitted to the acute care facility 120, the date they were transferred to the post-acute care facility 130, and/or other related dates. Although not shown, in some embodiments, report 500 includes each patient's respective risk features and/or risk feature scores. In some embodiments, the report 500 includes a predetermined number of risk features and/or risk feature scores. In some embodiments, the predetermined number (e.g., 1, 3, 5, etc.) of risk features and/or risk feature scores included in the report 500 are selected based the risk features and/or risk features scores that contributed the greatest amount to the risk score. For example, the report can include the top 5 risk features and/or risk feature scores for each patient. In some embodiments, report 500 includes one or explanations for the risk score, risk features, and/or risk feature scores.

As discussed with respect to FIG. 4, in some embodiments, the report 500 is linked or connected to one or more detailed reports for the subset of patients. In some embodiments, each patient is connected or linked to their respective detailed report that provides additional information about the patient (as discussed below in relation to FIG. 6). In some embodiments, selection of one or more of the patients in the report results in the detailed report for the selected patients to be displayed. For example, selection of Mr. Jones in report 500 causes the detailed report (FIG. 6) for Mr. Jones to be displayed.

FIG. 6 illustrates a detailed report for a respective patient in accordance with some embodiments. In some embodiments, detailed report 600 includes a data visualization that includes one or more data fields for particular patient. As described in relation to FIG. 5, in some embodiments, the data visualization is a spreadsheet, table, graph, chart, plot. In some embodiment, the one or more data fields include rows, columns, titles, legends, data points, etc. In some embodiments, the one or more data fields include a patients' name and/or identifier 602. For example, Mr. Jones' detailed report is displayed. In some embodiments, the detailed report for a particular patient is displayed in response to selection of their respective name and/or information in a report 500. For example, as described above, selection of Mr. Jones in report 500 causes the detailed report 600 for Mr. Jones to be displayed. In some embodiments, detailed report 600 includes one or more affordances 604 (e.g., links, buttons, or connection), that return a patient to the report 500.

In some embodiments, the detailed report 600 includes a patient's risk score, ranking 606, one or more risk features 608, one or more risk feature scores 610, and/or one or more risk feature explanations 612. In some embodiments, a predetermined number (e.g., 1, 3, 5, etc.) of risk features 608 and/or risk feature scores 610 with their respective risk explanation 612 are included in the detailed report 600. In some embodiments, the predetermined number of risk features 608 and/or risk feature scores 610 are listed by the highest contributing score to the lowest contributing score. For example, detailed report 600 incudes Mr. Jones' ranking 606 for the day and the top 5 risk features 608 (e.g. '5 Orders for "5-HT3 Receptor Antagonists' in last 30 days") their respective risk feature scores 610 (e.g., 16.40 percent) and risk explanation 612 (e.g., "Last Order: 'Ondansetron HCl' on 2019-1-25"). As explained above with respect to FIG. 3, in some embodiments, the one or more risk features 608 different elements or combinations of elements from the patient data. Similarly, determination of the risk feature scores 610 and the risk explanations 612 are described above in relation to FIG. 4. In some embodiments, the detailed report 600 include one or more note entry fields 614. In some embodiments, the note entry fields 614 enable medical practitioners (e.g., a physician or a nurse) to enter one or more action taken or notes for the one or more displayed risk features 608. In some embodiments, the inputs to the note entry fields 614 are used to update the patients risk score, risk feature scores, and/or risk explanations. In some embodiments, the inputs to the note entry fields 614 are used to update the patient data. In some embodiments, the inputs to the note entry fields 614 are provided to the one or more healthcare recording databases 110, acute care facilities 120, and/or post-acute care facilities.

In some embodiments, the detailed report 600 includes one more patient information data fields. In some embodiments, the one or more patient information fields include patient conditions 616 and patient specific collected data 618. For example, detailed report 600 includes a listing of a patient's conditions 616 (e.g., "active conditions") and patient specific collected data 618 (e.g., "vitals"). It should be noted that although detailed report 600 displays active conditions and vitals, any other information included in a patient's data (described above in relation to FIG. 1) can be included in the detailed report 600 depending on the information requested by the medical practitioners. In some embodiments, the detailed report 600 includes one or more dates 620 such that a medical practitioner is aware of when the information was collected, whether the information is current, and/or whether the information is outdated. In some embodiments, the detailed report 600 includes one or more data fields for medications and/or medical facility (acute 120 and/or post-acute 130 care facilities) updates 622. For example, detailed report 600 includes medications and/or medical facility updates 622 that specifies the medication (e.g. "Antibiotics") that a patient is provided, if any, ordered labs, and previously order labs, and/or type of labs. In some embodiments, the detailed report 600 includes one or more notification entry fields 624. In some embodiments, the notification entry fields 624 allow for a medical practitioner to request an alert or update when a patient event occurs (e.g., "Bowel Movement Alert"). In some embodiments, medical practitioner can customize the one or more notifications for a patient using the note entry field (discussed above in relation to FIG. 4).

In some embodiments, detailed report 600 includes a patient updates field 626. In some embodiments, the patient updates field 626 enables a medical practitioner to input one or more notes for a patient. The one or more notes input into the patient updates field 626 can be general notes that may or may not relate to one or more risk features or risk feature scores but that may contribute to a patient's risk score. In some embodiments, the one or more notes input into the patient updates field 626 are used to update a patient's risk score, risk features, risk feature scores, and/or risk explanation. In some embodiments, the one or more notes input into the patient updates field 626 are used to update the patient data. In some embodiments, the one or more notes input into the patient updates field 626 are provided to the one or more healthcare recording databases 110, acute care facilities 120, and/or post-acute care facilities.

FIGS. 7A-7E are flow charts illustrating a method 700 of generating and providing reports ranking patients at risk for readmission to an acute care facility from a post-acute care facility in accordance with some embodiments. In some embodiments, method 700 is performed by server 140 (e.g., server 140, FIGS. 1 and 2). Alternatively and/or additionally, in some embodiments, method 700 is performed by a remote device 150 (e.g., FIG. 1). Operations performed in FIG. 7 correspond to instructions stored in computer memory (e.g., memory 206 of server 140, FIG. 2, and/or memory of a remote device). In some embodiments, the methods are performed by a combination of the server 140 and remote device 150. In some instances and embodiments, the various operations of the methods described herein are interchangeable, and respective operations of the methods are performed by any of the aforementioned devices, systems, or combination of devices and/or systems. For convenience, the method operations will be described below as being performed by particular component or device, but should not be construed as limiting the performance of the operation to the particular device in all embodiments.

The server 140 receives (702) from the post-acute care facility, patient data for a plurality of patients. In some embodiments, the server 140 receives the patient data from one or more healthcare recording databases 110 or acute care facilities 120. In some embodiments, the patient data includes (704) one or more of: a medical condition, vital statistic, date, weight, blood sugar, oxygen saturation, pain identifier, medication, note, test order, and test result. In some embodiments, the patient data includes (706) recently collected patient data for each patient in the post-acute care facility. In some embodiments, the patient data includes (708) data collected from one or more patient wearable devices. In some embodiments, the patient data includes (710) patient one or more of socio-economic data, demographic data, diet data, air quality data, social visitor data, sleep data, and movement data. FIG. 1 provides further examples of the patient data that may be stored.

The server 140 inputs (712) the patient data for the plurality of patients into a risk machine-learning system that was previously trained using historical patient data and data reflecting any readmissions from one or more post-acute care facilities to one or more acute care facilities. Training of one or more risk machine-learning systems and models are described above in relation to FIG. 3. In some embodiments, the risk machine-learning system is based (714) on at least one of unsupervised learning, supervised learning, or semi-supervised learning techniques. In some embodiments, the acute care facility includes (716) hospitals, emergency rooms, surgical centers, intensive care units, and urgent care centers.

The server 140 determines (718), by the risk machine-learning system, a risk score for each patient of the plurality of patients based on each patient's patient data. Each risk score represents risk of a respective patient being readmitted to an acute care facility from the post-acute care facility. The server 140 generates (720), for display, the report including a list of at least a subset of patients from the plurality of patients, where the list is ranked from the patient with the highest risk of readmission to the patient with the lowest risk of readmission. In some embodiments, the report includes (722) respective patient risk scores for each of the patients in the subset of patients. For example, as illustrated in FIGS. 5 and 6, one or more reports can include a subset of the patients as well as the patients respective risk scores and/or rankings.

In some embodiments, for each patient of the subset of patients, the server 140 determines (724) one or more risk features that contributed to that patient's respective risk score. The report includes one or more respective risk features for each of the subset of patients. In some embodiments, for each of the one or more risk features, the server 140 determines (726) a risk feature score indicating how much that respective risk feature contributed to the risk score. The report includes, for each of the respective one or more risk features, that respective risk feature's risk feature score and ranks the one or more risk features by their respective risk feature scores from the highest score to the lowest. In some embodiments, the one or more risk features that contributed to that patient's respective risk score include (728) a respective explanation and the report includes a portion of the respective explanation for the one or more risk features. As described above in relation to FIG. 4, the risk score values determined by a risk machine-learning system can be broken down to individual risk features that contributed to the risk score. Similarly, the risk features can be analyzed to determine their contribution to the overall risk score. One or more risk explanations can be determined for the features and/or risk scores based on the inputs to the risk machine-learning system (the risk features), the patient data, and/or the risk scores.

In some embodiments, the report includes (730) one or more conditions for each of the plurality of patients. In some embodiments, the report includes (732) patient data for each of the plurality of patients. In some embodiments, the report includes (734) one or more note entry fields configured to receive input from a caregiver device. In some embodiments, input into a note entry field of the one or more note entry fields is receiving (736-a) and, in response to receiving the input into the note entry field, the server 140 updates (736-b) the patient data. In some embodiments, the input is received (e.g., via network 160) by one or more healthcare recording databases 110, acute care facility 120, post-acute care facility, and/or remote device 150 displaying the report.

In some embodiments, the report includes (738-a) one or more notification entry fields for receiving user defined notification requests. In some embodiments, a user defined notification request is received (738-b) into a notification entry field of the one or more notification entry fields and, in response to receiving the user defined notification request, the server 140 generates (738-c) a notification event based on the user defined notification request. A notification is provided upon occurrence of the notification event. In some embodiments, the input is received (e.g., via network 160) by one or more healthcare recording databases 110, acute care facility 120, post-acute care facility, and/or remote device 150 displaying the report. In some embodiments, the server 140 causes a remote device 150 to display an alert, sound a notification, and/or flag (e.g., highlight or color) relevant information based on the user defined notification request. In some embodiments, the notification event includes (740) a determination that a subsequent determined risk score for a respective patient is above a user defined risk threshold. In some embodiments, the notification event includes (742) a user specified time. In some embodiments, the notification event includes (744) a trigger based on an occurrence of one or more patient events.

In some embodiments, the server 140 generates (746) a separate detailed report for each patient of the subset of patients, where each detailed report for a respective patient of the subset of patients includes that respective patient's one or more risk features and corresponding one or more risk feature scores. For example, as shown in FIG. 6, server 140 generates a detailed report for the patients listed in report (e.g., a detailed report for Mr. Jones is generated).

In some embodiments, the subset of patients is determined (748) based on the plurality of patients with risk scores greater than a risk threshold. In some embodiments, the subset of patients includes (750) a predetermined number of patients with the highest risk scores from the plurality of patients. In some embodiments, the subset of patients includes (752) a predetermined number of patients that have been algorithmically determined. In some embodiments, the report includes (754) historical risk scores for each of the subset of patients. In some embodiments, server 140 displays (756) the report on a remote device. In some embodiments, the server 140 sends (758) the report to a remote device for display. In some embodiments, the report is configured (760) to display on an application installed on a remote device. In some embodiments, the report is a spreadsheet (762).

In some embodiments, the server 140 determines (764-a) whether the risk score for a respective patient of the subset of patients is above a notification threshold, and, in response to determining that the risk score is above the notification threshold, the server provides (764-b) a notification to a medical practitioner of the post-acute care facility to follow up with the patient. In this way, the server 140 is able to provide an emergency response to one or more physicians or nurses of a post-acute care facility 130. The notification alert can also ensure that a patient is checked on regularly if needed.

In some embodiments, the server 140 periodically retrains (766) the risk machine-learning system as new patient data, and data reflecting any readmissions from one or more post-acute care facilities to one or more acute care facilities, is collected. For example, as shown in FIGS. 3 and 4, feedback can be provided to improve, update, and retain risk machine-learning systems. In some embodiments, before the server 140 receives patient data for a plurality of patients, the server 140 receives (768-a) historical patient data from at least one healthcare recording database. The server 140 extracts (768-b) training data from the historical patient data. The server 140 utilizes (768-c) the training data to train multiple risk machine-learning systems. In some embodiments, the server 140 selects (768-d) a risk machine-learning system of the multiple risk machine-learning systems that respectively determined risk scores above a predetermined accuracy rate and stores (768-e) the risk machine-learning system. In some embodiments, the server 140 extracts (770-a) validation data from the historical patient data and, before storing the risk machine-learning system, inputs (770-b) the validation data into the machine-learning system. In some embodiments, the server 140 determines (770-c), by the risk machine-learning system, validation scores based on the validation data and updates (770-d) the risk machine-learning system based on validation scores. The above disclosed features relate to training and tuning a risk machine-learning system. Examples the training and tuning of a risk machine-learning system are provided in FIG. 3.

FIGS. 8A-8H illustrate a medical practitioner report for a particular patient in accordance with some embodiments. The medical practitioner report 800 includes, for display, collected patient data. In particular, in some embodiments, the medical practitioner report 800 includes ranking information and/or patient information as described above with reference to FIGS. 5 and 6. In some embodiments, the medical practitioner report 800 for a patient is generated and displayed in response to selection of the patient's name and/or information in a patient listing or ranking (e.g., report 500; FIG. 5). In some embodiments, medical practitioner report 800 is associated with a ranking for the patient.

The medical practitioner report 800 includes the patient's name (or pseudonym to protect the patient's privacy), patient identifier (or number), patient location (e.g., facility, room number, bed number, etc.), and report date. The medical practitioner report 800 includes one or more sections. In some embodiments, the one or sections include an overview section 802, vitals section 804, lab results section 806, risks section 808, highlights section 810, diagnosis, medications, and orders sections 812, and progress notes section 814. In some embodiments, the medical practitioner report 800 includes information for identifying post-acute care or chronic long-term admissions.

Figure 8A:
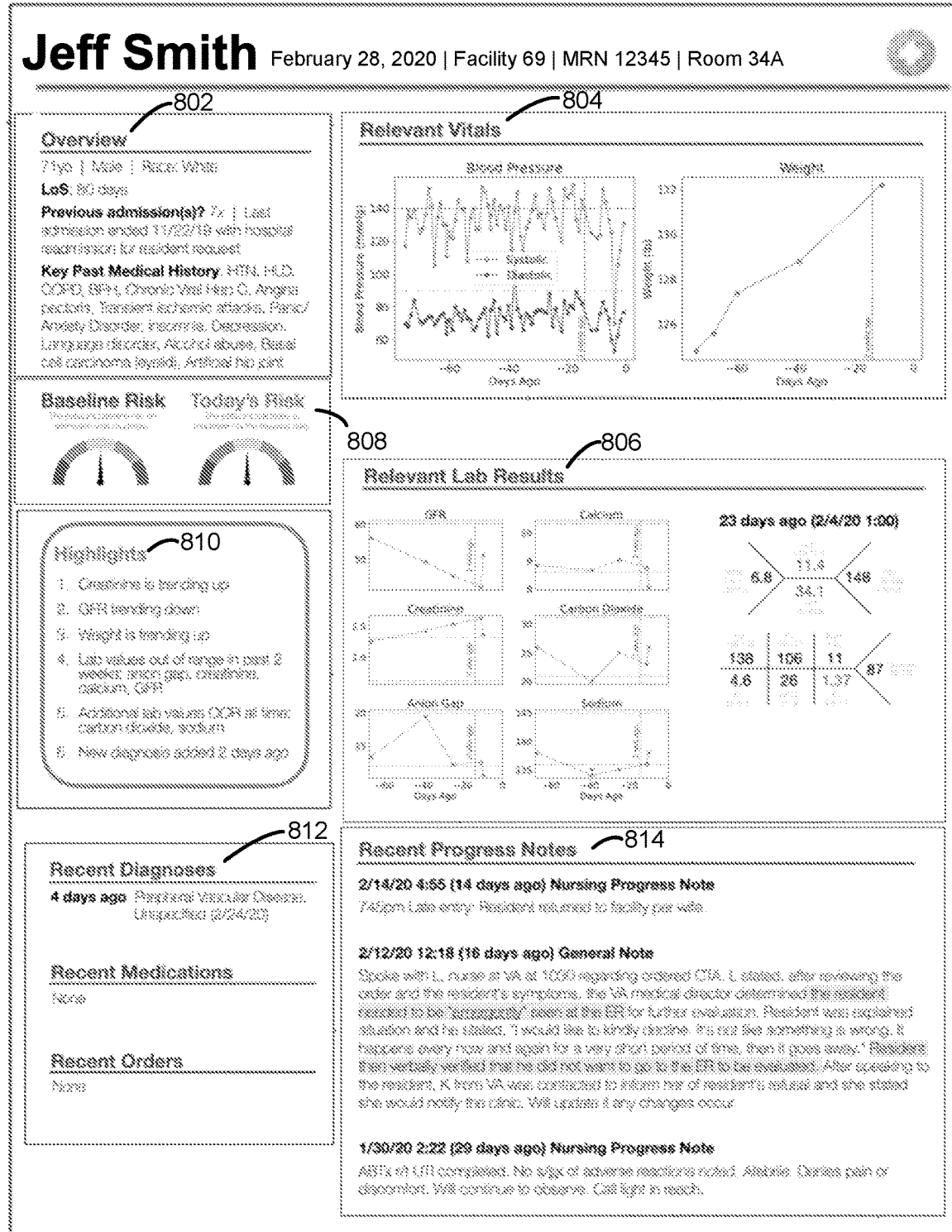
FIG. 8A illustrates a medical practitioner report, in accordance with some embodiments.
Figure 8B:
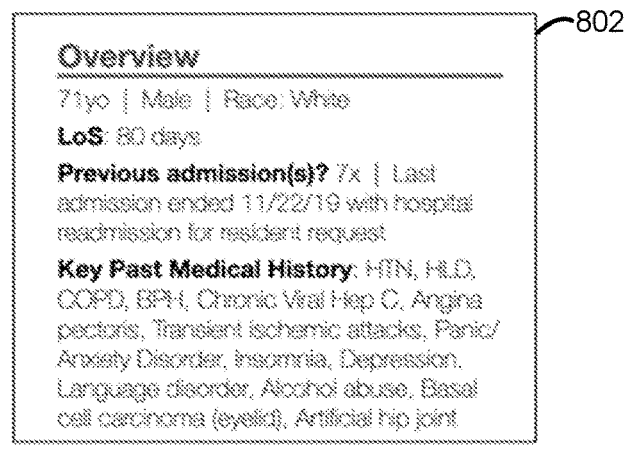
FIGS. 8B-8H illustrates different sections of the medical practitioner report, in accordance with some embodiments.

The overview section 802 is shown in FIG. 8B. The overview section 802 provides a snapshot (or summary) of the patient's information. In some embodiments, the overview section 802 includes the patient's age, sex, and/or race. In some embodiments, the overview section 802 includes the patient's length of stay (LoS), such as the number of hours, days, months, etc. that the patient has been at the medical facility (e.g., post-acute care facility). As an example, the patient ("Jeff Smith") is a 71-year-old male that has been at the facility for 80 days. In some embodiments, the overview section 802 includes information regarding a patient's previous admission to one or more facilities. For example, the overview report 802 can include the number of times that the patient has been admitted to the facility (e.g., "7×"), how the previous admission ended (e.g., released, readmitted to an acute care facility, etc.), what the previous admission was for (e.g., acute conditions, chronic condition, etc.), where the patient was admitted from (e.g., acute care facility to post-acute care facility, residence to post-acute care facility, etc.). In some embodiments, the overview section 802 identifies whether the current admission is for post-acute care, chronic long term care, etc.

In some embodiments, the overview section 802 includes the patient's medical history. For example, the medical history can include chronic or acute conditions or illnesses, diseases, mental conditions, disorders, and other patient data collected (as described herein). In some embodiments, acute conditions or illnesses for the current stay (or admission) are included with the other medical history (e.g., excluding acute conditions or illnesses from previous admissions). In some embodiments, one or more reasons for the patient's admission to the facility are included in the overview section 802. The one or more reasons (or explanations) are generated by a risk model application module 224 as described above with reference to FIG. 2 and FIG. 4. In some embodiments, the one or more reasons are based on clinical notes for the patient (e.g., progress notes section 814 or other notes in the patients collected data). In some embodiments, long ICD-10 (International Classification of Diseases, Tenth Revision) codes are converted to shorthand acronyms to allow for more information to be included in the overview section 802.

Figure 8C:
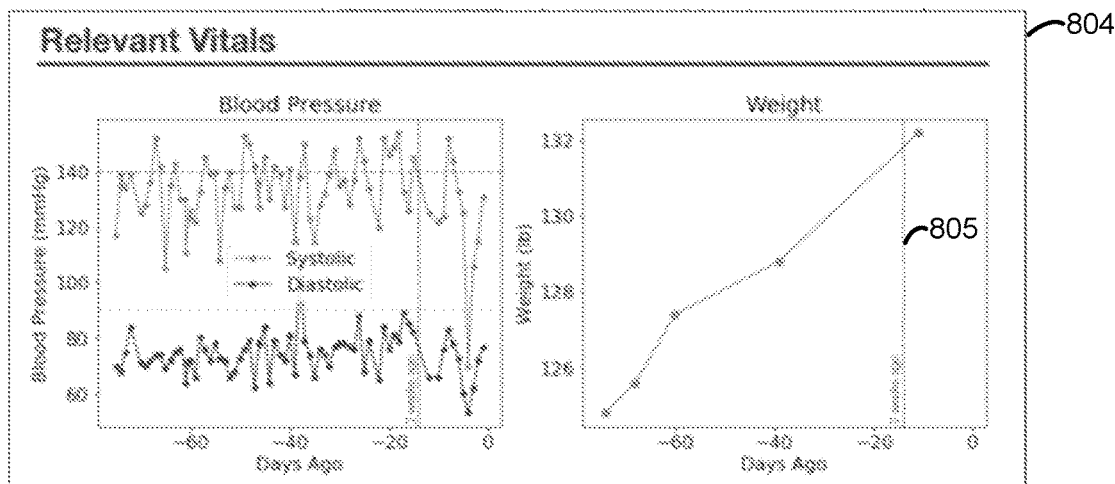

Turning to FIG. 8C, the vitals section 804 includes patient data related to the patient's vital information (vitals, e.g., blood pressure, weight, oxygen saturation, pulse, etc.). In some embodiments, the vitals section 804 includes one or more data visualizations for the patient data, as described above in reference to FIG. 5, data visualizations include data fields, spreadsheets, tables, graphs, charts, plots, fishbone diagrams, etc. In some embodiments, the data visualizations of the vitals section 804 include data over a predetermined period of time (e.g., 10 days, 14 days, 30 days, 80 days, etc.). In some embodiments, the data visualizations include one or more markers 805 such as min/max thresholds, time windows (e.g., two weeks ago), etc.

In some embodiments, the vitals section 804 includes one or more data visualizations for vitals that are out of range (exceed or fall below a medical practitioner defined (min/max) threshold), trending upwards or downward, or are relevant to the patient given their medical history. For example, the vitals section 804 can include a data visualization for blood pressure for a patient with low blood pressure and that has had her blood pressure trending downward over the past two weeks. In another example, a medical practitioner may specify that a patient losing 5 pounds a week (i.e., a medical practitioner defined threshold) increases the patient's risk of being readmitted to an acute care facility (or serious harm), and the vitals section 804 can include a data visualization for the patient's weight (over a predetermined period of time) when the patient's weight loss for a given week meets or exceeds 5 pounds. The vitals section 804 improves the medical practitioner's ability to interpret and analyze complicated data by identifying reliable trends is the patient data.

Figure 8D:
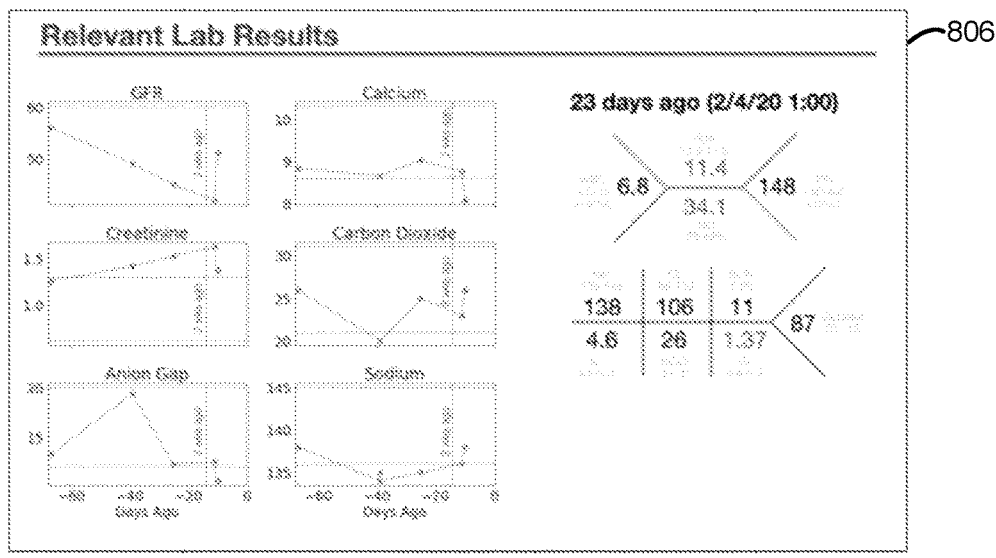

As shown in FIG. 8D, the lab results section 806 includes one or more lab results for the patient. In some embodiments, the one or more lab results include one or more data visualizations (as described above). In some embodiments, lab results section 806 include data visualizations for lab results that are out of range (exceed or fall below a medical practitioner defined (min/max) threshold), trending upwards or downward, or are relevant to the patient given their medical history. In some embodiments, if more than two lab values are available, a plot is shown and the most recent values are shown in a fishbone diagram. In some embodiments, the data visualizations of the lab results section 806 include data over a predetermined period of time and include one or more markers as discussed above with reference to FIG. 8C. Like the vitals section 804, the lab results section 806 improves the medical practitioner's ability to interpret and analyze complicated data by identifying reliable trends in the patient data.

Figure 8E:

FIG. 8E illustrates the risks section 808. In some embodiment, the risks section 808 includes a baseline risk and a current risk for the day ("today's risk"). In some embodiments, the baseline risk is based on relatively static patient data. Static patient data includes patient data that does not vary on a daily basis or per each measurement. A non-exhaustive list of static patient data includes chronic medical conditions, diseases, illnesses, age, sex, etc. The current risk for the day is based on dynamic patient data. Alternatively, in some embodiments, the current risk for the day is based on a combination of dynamic patient data and static patient data. Dynamic patient data includes data that can vary on a daily basis or per each measurement. A non-exhaustive list of dynamic patient data includes blood pressure, weight, temperature, diet, skin assessment (e.g., rashes, discoloration, etc.), lung conditions, clinical notes, blood sugar, etc. The baseline risk and the current risk for the day are determined by the risk model application module 224 as described above in reference to FIG. 2 and FIG. 4. The baseline risk and the current risk for the day can be determined by the same and/or distinct risk models.

In some embodiments, the baseline risk and the current risk for the day are each represented as a meter 809. In some embodiments, the meter includes a plurality of levels, each higher level indicating the patient's increased risk. In some embodiments, each level of the plurality of levels is color-coded. For example, the plurality of levels can include a no risk to low risk level (green), low to medium risk level (yellow green), medium risk level (yellow), medium to high risk level (orange), high risk level (red). In some embodiments, the current risk for the day is described as a factor of the baseline risk. For example, the current risk for the day can be described as 1 time, 2 times, 3.5 times, 5 times, etc. of the baseline risk.

Figure 8F:
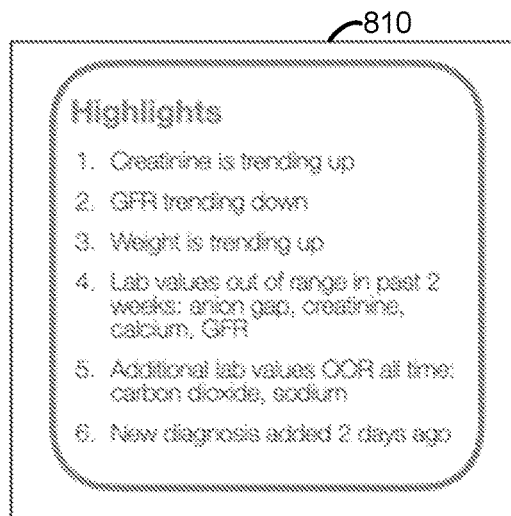

The highlights section 810 is shown in FIG. 8F. The highlights section 810 summarizes one or more risk features. In particular, the highlights section 810 includes a listing of risk features that contributed to the patient's risk (e.g., the baseline risk and/or the current risk for the day). In some embodiments, the one or more risk features in the highlights section 810 are ranked in order from the risk features that contributed the most the patient's risk to the risk features that contributed the least. In some embodiments, the highlights section 810 includes a predetermined number of risk features (e.g., the top 5, 10, 15, etc. risk features). In this way, the medical practitioner is provided with the top contributing risk features without being overwhelmed by risk features that contributed the least to the patient's risk. In some implementations, the highlights section 810 includes explanations for the one or more risk features.

The explanations for the one or more risk features are generated by risk explanation module 230 of the machine-learning system described above in reference to FIGS. 2 and 4. More specifically, the risk explanation module 230 utilizes the complex (and typically indecipherable) patterns, calculations, and/or solutions determined or identified by the machine-learning system (see e.g., FIGS. 2-4) to generate human readable and understood explanations. The explanations generated by the risk explanation module 230 are optimized to emphasize relevant information without overloading a medical practitioner with information. In some embodiments, each risk feature identified in the highlights section 810 includes a corresponding risk feature explanation. The risk feature explanations assist medical practitioners in identifying abnormal values or trends, potential lapses in care, and/or any other factors that flagged the patient at risk. Abnormal values include outlier data for a particular patient (e.g., patient data that is too high, too low, inconsistent). Trends include patient data that increases, decreases, or remains constant over time (e.g., temperature, body weight, blood sugar, etc.). Potential lapses in care may include medication dosages that a patient is receiving, combination of medications a patient is receiving, the patient's most reason lab results or checkup, a patient's diet, and/or any other lapse identifier by the machine-learning system. The above-examples are non-exhaustive and provide a generalized overview of the risk explanations generated by the risk explanation module 230 using the complex patterns, calculations, and/or solutions determined by the machine-learning system.

As an additional example, the risk feature explanations can include a human readable message indicating that a patient has not had a particular exam within predetermined period of time (e.g., patient has not lab tests performed in the last two weeks). As another example, the risk feature explanations can include a human readable message indicating the patient's lab results are trending upwards (e.g., creatine is trending upwards). In some embodiments, risk feature explanations are based on a single risk feature (e.g., patient data, such as blood pressure, exceeded a min/max threshold). Alternatively or additionally, in some embodiments, the risk feature explanations are based on a combination of risk features and/or other patient data. For example, a non-exhaustive list of combinations includes: a particular medication that a patient is taking and the patient's temperature (e.g., patient has a fever), the patient's blood pressure and diseases, the patient's age and the temperature outside (e.g., humid hot day), air pollution and a patient's lung conditions (e.g., patient is congested), and/or any other combination of two or more risk features and/or other patient data. In some embodiments, the risk feature explanations are based on one or more risk features, patient data, identified trends in time-series, and/or other sources of data, such as relevant information from clinical notes (extracted and analyzed through natural language processing (NLP)

techniques); environmental data; region specific conditions; new reports (e.g., increased influenza report); etc.

In some embodiments, the risk feature explanations are determined for each disease of a patient. For example, a patient with congestive heart failure (CHF) and chronic obstructive pulmonary disease (COPD), can have a first set of risk feature explanations determined for CHF and a second set of risk feature explanations determined for COPD. In some embodiments, the first set of risk features for the first disease and the second set of risk features for the second disease can be combined resulting in an overall risk explanation that accounts for both the first and second disease.

In some embodiments, the highlights section 810 can include a recommended action (or treatment) for the identified risk features. For instance, if a risk feature indicates that a patient has not had lab tests performed in the last two weeks, the highlights section 810 may recommend scheduling or ordering lab tests for the patient. As another example, the risk features may identify that the patient's blood sugar is abnormal and can recommend a change to the patient's diet. In some embodiments, the recommended actions can include a message to the medical practitioner to pay closer attention to the patient or certain abnormalities in the patient's data. The examples provided above are non-limiting. In some embodiments, the recommended actions are based on the risk features and/or the corresponding explanations for the risk features. Alternatively or additionally, in some embodiments, the recommended actions are based on the baseline risks and the current risk for the day of a patient.

The risk features, the corresponding explanations, and/or the recommended actions are determined by the risk model application module 224 as described above in reference to FIG. 2 and FIG. 4.

Figure 8G:
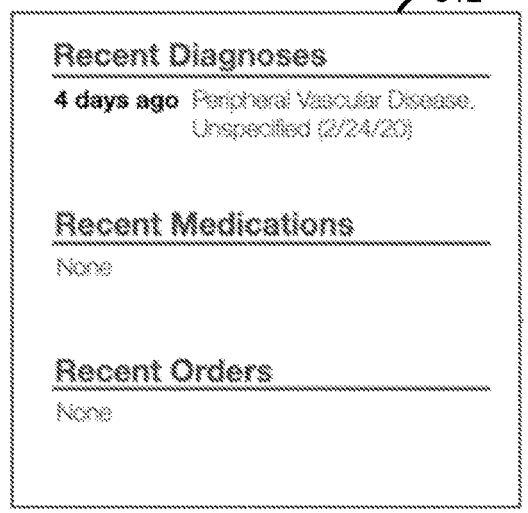

Turning to FIG. 8G, the diagnosis, medications, and orders sections 812 are shown. The diagnosis, medications, and orders sections 812 include any new diagnoses, medications, or orders within a predetermined period (e.g., the past 7 days, 14 days, 30 days, etc.). Orders, in some embodiments, include exams, appointments, test, or other medical procedures scheduled for the patient. In some embodiments, diagnosis, medications, and orders sections 812 identity when diagnoses, medications, or orders were made. In some embodiments, the diagnosis, medications, and orders sections 812 identity how long a patient has had the identified diagnoses, medications, or orders.

Figure 8H:
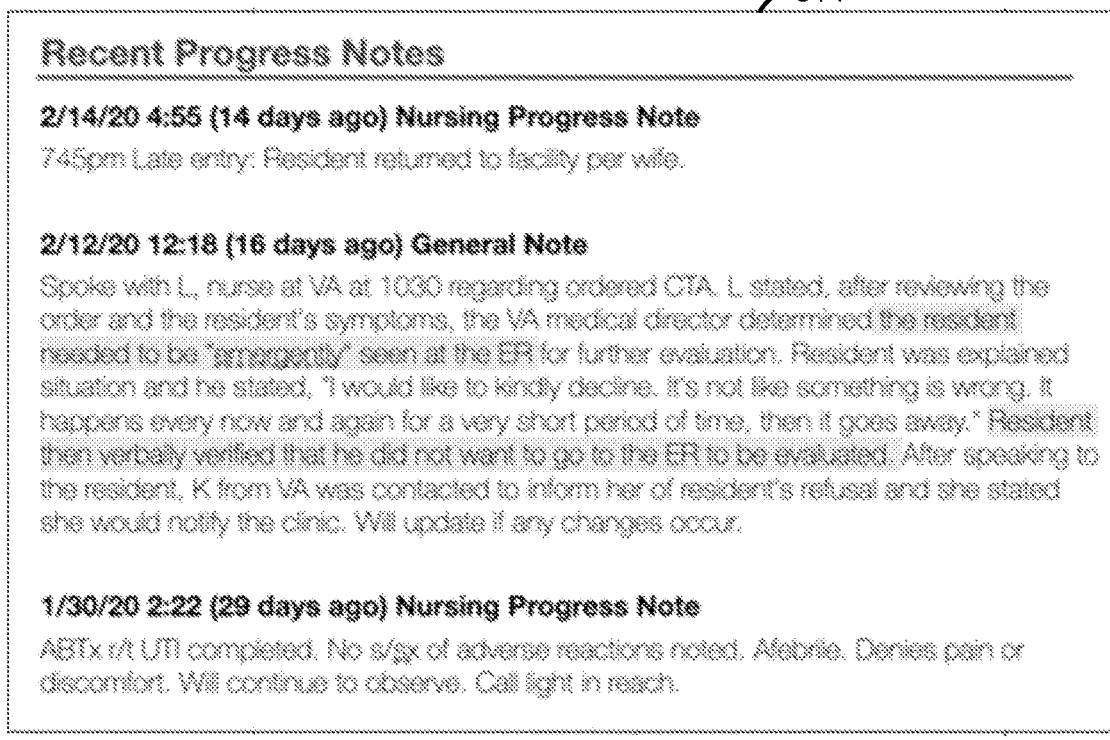

The progress notes section 814 is shown in FIG. 8H. The progress notes section 814 includes clinical notes for the patient added by a caregiver. In some embodiments, the clinical notes are for a predetermined period of time (e.g., the past 7 days, 14 days 30 days, etc.). The progress notes section includes patient symptoms, physical exam findings, and/or care plans. In some embodiments, NLP is performed on the clinical notes to identify and highlight symptoms, physical exam findings, and/or other findings in the clinical notes. For example, if the clinical notes indicate that the patient was in severe pain, that portion of the clinical notes can be highlighted. As another example, the clinical notes can indicate that the patient requested to go to the emergency room, and the patient's request can be highlighted.

In some embodiments, NLP is performed on the clinical notes to extract relevant information. A non-exhaustive list of extracted information includes history of present illness (HPI), supplemental patient data over time (e.g., oxygen information and tracking the oxygen information (e.g., upward and/or downward trend)), PRN med administration and tracking of the PRN med administration over time. In some embodiments, the extracted relevant information is provided to one or more risk models (e.g., risk model application module 224; FIG. 2 and FIG. 4) to determine the patient's risk (e.g., the baseline risks and the current risk for the day of a patient), one or more risk features for the patient, and/or one or more explanations for the patient's risk and/or one or more risk features. In some implementations, the extracted relevant information is provided to the risk model application module 224 to determine a recommended action (as described above with reference to FIG. 8F). For example, if the clinical notes indicate that a painkiller has already been administered to the patient, the recommended action will forgo recommending that the patient be given another painkiller (e.g., if the patient has recently been given the painkiller or reached her daily maximum allowance for the painkiller (i.e., medical practitioners defined threshold)). In some embodiments, the NLP results are used as feedback to improve subsequent NLP of future clinical notes.

The medical practitioner report 800 and the one or more sections of the medical practitioner report 800 are generated (for display) by the report generating module 232 described above with reference to FIG. 2 and FIG. 4.

FIG. 9 illustrates an additional medical practitioner report for a particular patient in accordance with some embodiments. The additional medical practitioner report 900 in an instance of the detailed report 600 (FIG. 6) and the medical practitioner report 800 (FIG. 8A-8H) described above. The additional medical practitioner report 900 includes, for display, collected patient data. In particular, in some embodiments, the additional medical practitioner report 900 includes ranking information and/or patient information as described above with reference to FIGS. 5, 6, and 8A-8H.

The additional medical practitioner report 900 includes patient information 902 such as one or more of the patient's name (or pseudonym to protect the patient's privacy), patient identifier (or number), patient location (e.g., facility, room number, bed number, etc.), patient risk ranking, patient demographic information, report date, and other patient specific data. The additional medical practitioner report 900 includes one or more sections. In some embodiments, the one or sections such as a vitals section 804, lab results section 806, risks section 808, highlights section 810, diagnosis, medications, and orders sections 812, and progress notes section 814. In some embodiments, the medical practitioner report 800 includes information for identifying post-acute care or chronic long-term admissions. Additional information on the one or more section is provided above in reference to FIGS. 8A-8H.

The foregoing description, for purpose of explanation, has been described with reference to specific embodiments. However, the illustrative discussions above are not intended to be exhaustive or to limit the embodiments to the precise forms disclosed. Many modifications and variations are possible in view of the above teachings. The embodiments were chosen and described in order to best explain the principles and their practical applications, to thereby enable others skilled in the art to best utilize the embodiments and various embodiments with various modifications as are suited to the particular use contemplated.

It will also be understood that, although the terms first, second, etc. are, in some instances, used herein to describe various elements, these elements should not be limited by these terms. These terms are used only to distinguish one element from another. For example, a first client device could be termed a second client device, and, similarly, a second client device could be termed a first client device, without departing from the scope of the various described embodiments. The first client device and the second client device are both client devices, but they are not the same client device.

The terminology used in the description of the various embodiments described herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is, optionally, construed to mean "when" or "upon" or "in response to determining" or "in response to detecting" or "in accordance with a determination that," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]" or "in accordance with a determination that [a stated condition or event] is detected," depending on the context.

What is claimed is:

1. A method of generating an interactable report that ranks patients at risk for readmission to an acute care facility from a post-acute care facility and provides guidance for reducing the risk of readmission, the method comprising:
   at a computer system having one or more processors and memory storing one or more programs that are executable by the computer system:
      receiving, from the post-acute care facility and a healthcare recording system, patient data for a plurality of patients, including medical history and textual input from a caregiver;
      converting, by the risk machine-learning system, at least some of the patient data into expected patient data with predetermined input formats and predetermined features;
      inputting the expected patient data for the plurality of patients into the risk machine-learning system that was previously trained using historical patient data and data reflecting any readmissions from one or more post-acute care facilities to one or more acute care facilities;
      determining, by the risk machine-learning system, a risk score for each patient of the plurality of patients based on each patient's expected patient data, wherein each risk score is based on one or more risk features that contribute to a risk score for a respective patient being readmitted to an acute care facility from the post-acute care facility;
      generating an interactable report comprising a list of at least a subset of patients from the plurality of patients, wherein (i) the interactable report is generated with a predetermined report format, and (ii) the subset of patients are:

ranked from a patient with the highest risk of readmission to a patient with the lowest risk of readmission, and associated with respective reports generated by the risk machine-learning system that include the one or more risk features and associated risk feature explanations that provide i) an explanation of the risk feature and ii) an explanation of the interaction between at least two risk features;

sending the interactable report to a remote device for display; and causing display of the interactable report at the remote device, the interactable report including an entry field for receiving additional textual input, such that the additional textual input, when received, is added to the patient data in real-time.

2. The method of claim 1, wherein the interactable report includes respective patient risk scores for each of the patients in the subset of patients.

3. The method of claim 1, wherein risk feature explanations describe the respective risk feature's contribution to the risk score.

4. The method of claim 1, further comprising: for each of the one or more risk features, determining a risk feature score indicating how much that respective risk feature contributed to the risk score, wherein the respective reports include, for each of the respective one or more risk features, that respective risk feature's risk feature score.

5. The method of claim 1, wherein the risk score for each patient of the subset of patients includes a summary explanation and the interactable report includes a portion of the summary explanation.

6. The method of claim 5, wherein the summary explanation is based on one or more of the one or more risk features, patient data trends, patient data patterns, and other sources of data.

7. The method of claim 1, wherein the respective reports include one or more conditions for a patient.

8. The method of claim 1, wherein the interactable report includes patient data for each of the plurality of patients.

9. The method of claim 1, further comprising:
in response to receiving additional textual input at the entry field, determining an updated risk score for each patient of the plurality of patients.

10. The method of claim 1, wherein the interactable report includes one or more notification entry fields for receiving user defined notification requests; and
the method further comprises:
receiving a user defined notification request into a notification entry field of the one or more notification entry fields; and
in response to receiving the user defined notification request, generating a notification event based on the user defined notification request, wherein a notification is provided upon occurrence of the notification event.

11. The method of claim 10, wherein the notification event includes determining that a subsequent determined risk score for a respective patient is above a user defined risk threshold.

12. The method of claim 1, wherein the subset of patients comprises a predetermined number of patients with the highest risk scores from the plurality of patients.

13. A system for generating an interactable report that ranks patients at risk for readmission to an acute care facility from a post-acute care facility and provides guidance for reducing the risk of readmission, the system comprising:

one or more processors; and
memory storing instructions for execution by the one or more processors, the instructions including instructions for:
receiving, from the post-acute care facility and a healthcare recording system, patient data for a plurality of patients, including medical history and textual input from a caregiver;
converting, by the risk machine-learning system, at least some of the patient data into expected patient data with predetermined input formats and predetermined features;
inputting the expected patient data for the plurality of patients into the risk machine-learning system that was previously trained using historical patient data and data reflecting any readmissions from one or more post-acute care facilities to one or more acute care facilities;
determining, by the risk machine-learning system, a risk score for each patient of the plurality of patients based on each patient's expected patient data, wherein each risk score is based on one or more risk features that contribute to a risk score for a respective patient being readmitted to an acute care facility from the post-acute care facility;
generating an interactable report comprising a list of at least a subset of patients from the plurality of patients, wherein (i) the interactable report is generated with a predetermined report format, and (ii) the subset of patients are:
ranked from a patient with the highest risk of readmission to a patient with the lowest risk of readmission, and
associated with respective reports generated by the risk machine-learning system that include the one or more risk features and associated risk feature explanations that provide i) an explanation of the risk feature and ii) an explanation of the interaction between at least two risk features; and
sending the interactable report to a remote device for display; and
causing display of the interactable report at the remote device, the interactable report including an entry field for receiving additional textual input, such that the additional textual input, when received, is added to the patient data in real-time.

14. The system of claim 13, wherein the interactable report includes respective patient risk scores for each of the patients in the subset of patients.

15. The system of claim 1, wherein risk feature explanations describe the respective risk feature's contribution to the risk score.

16. The system of claim 13, the risk score for each patient of the subset of patients includes a summary explanation and the interactable report includes a portion of the summary explanation.

17. The system of claim 16, wherein the summary explanation is based on one or more of the one or more risk features, patient data trends, patient data patterns, and other sources of data.

18. A non-transitory computer-readable storage medium having instructions stored thereon for generating an interactable report that ranks patients at-risk for readmission to an acute care facility from a post-acute care facility and provides guidance for reducing the risk of readmission, wherein the instructions, when executed by one or more processors of a device, cause the device to perform operations comprising:
receiving, from the post-acute care facility and a healthcare recording system, patient data for a plurality of patients, including medical history and textual input from a caregiver;
converting, by the risk machine-learning system, at least some of the patient data into expected patient data with predetermined input formats and predetermined features;
inputting the expected patient data for the plurality of patients into the risk machine-learning system that was previously trained using historical patient data and data reflecting any readmissions from one or more post-acute care facilities to one or more acute care facilities;
determining, by the risk machine-learning system, a risk score for each patient of the plurality of patients based on each patient's expected patient data, wherein each risk score is based on one or more risk features that contribute to a risk score for a respective patient being readmitted to an acute care facility from the post-acute care facility;
generating an interactable report comprising a list of at least a subset of patients from the plurality of patients, wherein (i) the interactable report is generated with a predetermined report format, and (ii) the subset of patients are:
ranked from a patient with the highest risk of readmission to a patient with the lowest risk of readmission, and
associated with respective reports generated by the risk machine-learning system that include the one or more risk features and associated risk feature explanations that provide an explanation of the risk feature and ii) an explanation of the interaction between at least two risk features;
sending the interactable report to a remote device for display; and
causing display of the interactable report at the remote device, the interactable report including an entry field for receiving additional textual input, such that the additional textual input, when received, is added to the patient data in real-time.

* * * * *